US006972297B2

(12) United States Patent
Brooks et al.

(10) Patent No.: US 6,972,297 B2
(45) Date of Patent: Dec. 6, 2005

(54) 2-HYDROXY-MUTILIN CARBAMATE DERIVATIVES FOR ANTIBACTERIAL USE

(75) Inventors: Gerald Brooks, Harlow (GB); Eric Hunt, Harlow (GB); Steven Howard, Harlow (GB)

(73) Assignee: SmithKline Beecham p.l.c., Brentford (GB)

( * ) Notice: Subject to any disclaimer, the term of this patent is extended or adjusted under 35 U.S.C. 154(b) by 282 days.

(21) Appl. No.: 10/240,908

(22) PCT Filed: Mar. 29, 2001

(86) PCT No.: PCT/EP01/03594

§ 371 (c)(1), (2), (4) Date: Oct. 4, 2002

(87) PCT Pub. No.: WO01/74788

PCT Pub. Date: Oct. 11, 2001

(65) Prior Publication Data

US 2003/0114674 A1 Jun. 19, 2003

(30) Foreign Application Priority Data

Apr. 4, 2000 (GB) ............................................. 0008260
Nov. 4, 2000 (GB) ............................................. 0027182

(51) Int. Cl.[7] ..................... C07D 211/98; C07D 211/94; C07D 237/20; A61K 31/44; A61P 31/04

(52) U.S. Cl. ....................... 514/355; 514/357; 546/285; 546/206; 560/256; 544/281; 544/294; 544/410; 544/350; 544/224; 548/194

(58) Field of Search .......................... 546/285; 514/355, 514/357; 560/256

(56) References Cited

FOREIGN PATENT DOCUMENTS

| | | |
|---|---|---|
| AU | 774419 | 2/2002 |
| FR | 2 771 008 | 5/1999 |
| WO | WO 97/25309 | 7/1997 |
| WO | WO 98/05659 | 2/1998 |
| WO | WO 99/21855 | 5/1999 |
| WO | WO 00/07974 | 2/2000 |

OTHER PUBLICATIONS

Berner, et al., "Chemie der Pleuromutiline, 3. Mitt. Synthese des 14–0–Acetyl–19,20–dihydro–A–nor–mutilins", (1981), Monatshefte fur Chemie, 112, pp. 1441–1450.

Schulz et al., "Chemie der Pleuromutiline–VI...", (1984), Tetrahedron, 40(5), pp. 905–917.

*Primary Examiner*—Mark L. Berch
*Assistant Examiner*—Kahsay Habte
(74) *Attorney, Agent, or Firm*—Linda E. Hall; Stephen Venetianer; Charles M. Kinzig

(57) ABSTRACT

2-(S)-hydroxymutilin carbamate derivatives of formula (I), in which $R^1$ is a 5- or 6-membered optionally substituted heteroaryl group; and $R^2$ is vinyl or ethyl, are useful in the treatment of bacterial infections (I)

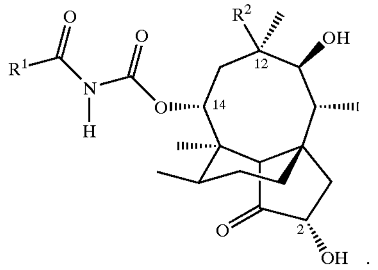

9 Claims, No Drawings

2-HYDROXY-MUTILIN CARBAMATE DERIVATIVES FOR ANTIBACTERIAL USE

The present invention relates to novel compounds, to processes for their preparation, to pharmaceutical compositions containing them and to their use in medical therapy, particularly antibacterial therapy.

Pleuromutilin, the compound of formula (A), is a naturally occurring antibiotic which has antimycoplasmal activity and modest antibacterial activity. Mutilin and other compounds with a free OH at C-14 are inactive. The impact of further modification at C-14 on the activity of pleuromutilin has been investigated (H. Egger and H. Reinshagen, *J. Antibiotics*, 1976, 29, 923). Replacing the hydroxy group of the glycolic ester moiety at position 14 by another O, S or N-linked group was found to improve anti-microbial activity. Thus, introducing a diethylaminoethylthio group gives the compound of formula (B), also known as Tiamulin, which is used as a veterinary antibiotic (G. Hogenauer in *Antibiotics*, Vol. V, part 1, ed. F. E. Hahn, Springer-Verlag, 1979, p.344).

(A)

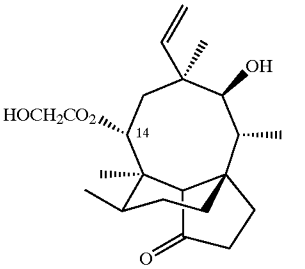

(B)

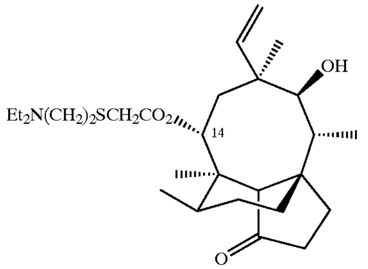

In this application, the non-conventional numbering system which is generally used in the literature (G. Hogenauer, loc. cit.) is used.

WO 97/25309 (SmithKline Beecham) describes further modification of the acyloxy group, disclosing inter alia 14-O-acylcarbamoyl ($R^aCONR^bCO_2$—) derivatives of mutilin in which $R^a$ may have a range of values, including optionally substituted heterocyclic and $R^b$ is a selected from a variety of monovalent groups.

WO 98/05659 (SmithKline Beecham) describes further 14-O-carbamoyl derivatives of mutilin in which the N-atom of the carbamoyl group is acylated by a group which includes an azabicyclic moiety.

WO 99/21855 (SmithKline Beecham) describes further derivatives of mutilin or 19,20-dihydromutilin, in which the glycolic ester moiety at position 14 is modified. In such compounds, the 2 position (a to the ketogroup) may be substituted by hydroxy. The vast majority of the compounds exemplified therein, however, do not have such a substituent.

In addition 19,20-dihydro-2α-hydroxy-mutilin is described by G. Schulz and H. Berner in *Tetrahedron*, 1984, vol. 40, pp 905–917.

The present invention is based on the unexpected discovery that certain novel 14-O-carbamoyl derivatives mutilin derivatives further having a (2S)-hydroxy substituent have potent antimicrobial activity.

Accordingly the present invention provides a compound of formula (I):

(I)

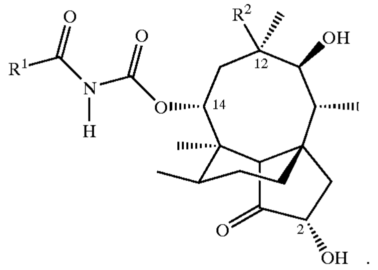

in which:

$R^1$ is a 5- or 6-membered optionally substituted heteroaryl group; and $R^2$ is vinyl or ethyl.

In this series of compounds, the introduction of a (2S)-hydroxy substituent is found to impart greater metabolic stability towards liver enzymes than the corresponding 2-unsubstituted counterparts.

Examples of heteroaryl groups for $R^1$ include those having a 5 or 6-membered single ring comprising 1 or 2 nitrogen atoms and optionally comprising a further heteroatom selected from oxygen or sulphur, for example pyridine, pyridazine, pyrimidine, pyrazine, isoxazole, thiazole, imidazole, pyrazole; or a 5 or 6-membered ring comprising 3 nitrogen atoms, for example, 1,2,3-triazole, 1,2,4-triazole; or a 5 or 6-membered ring comprising 1 or 2 nitrogen atoms fused to a benzene ring, for example, benzimidazole. Further examples of heteroaryl groups for $R^1$ include those having a 5 or 6-membered ring comprising 1 or 2 nitrogen atoms fused to a second 5 or 6-membered optionally substituted heteroaryl ring comprising 1 or 2 nitrogen atoms.

Representative examples of such heteroaryl groups for $R^1$ include, for example, pyridine, pyrazine, pyridazine, 3-oxo-3,4-dihydropyrido[2,3-b]pyrazine, pyrazolo[1,5-a]pyrimidine, pyrimidine, and thiazole. Preferred examples of such heteroaryl groups for $R^1$ include, for example, pyridine, pyrimidine, and thiazole.

Representative optional substituents for $R^1$ include amino, mono- or di-$(C_{1-6})$alkylamino, $(C_{1-6})$alkyl, $(C_{1-6})$alkoxy, nitro and N-containing heterocyclyl such as piperidin-4-yl which may be optionally substituted. Typically $R^1$ may comprise one or two substituents.

When used herein, the term "aryl" refers to, unless otherwise defined, phenyl or naphthyl. A substituted aryl group comprises up to five, preferably up to three substituents.

Suitable substituents for an aryl group, including phenyl when forming part of a benzyl group, include, for example, and unless otherwise defined, halogen, $(C_{1-6})$alkyl, aryl, aryl$(C_{1-6})$alkyl, $(C_{1-6})$alkoxy, $(C_{1-6})$alkoxy$(C_{1-6})$alkyl, halo$(C_{1-6})$alkyl, aryl$(C_{1-6})$alkoxy, hydroxy, nitro, cyano, azido, amino, mono- and di-N-$(C_{1-6})$alkylamino, acylamino, arylcarbonylamino, acyloxy, carboxy, carboxy salts, carboxy esters, carbamoyl, mono- and di-N-$(C_{1-6})$alkylcarbamoyl, $(C_{1-6})$alkoxycarbonyl, aryloxycarbonyl, ureido, guanidino, $(C_{1-6})$alkylguanidino, amidino, $(C_{1-6})$alkylamidino, sulphonylamino, aminosulphonyl, $(C_{1-6})$alkylthio, $(C_{1-6})$alkylsulphinyl, $(C_{1-6})$alkcylsulphonyl, heterocyclyl, heteroaryl, heterocyclyl($C_{1-6}$)alkyl and heteroaryl($C_{1-6}$)alkyl. In addition, two adjacent ring carbon atoms may be linked by a ($C_{3-5}$)alkylene chain, to form a carbocyclic ring.

When used herein, the terms "alkyl" and "alkenyl" refer to (individually or as part of alkoxy or alkenyloxy) straight and branched groups containing up to six carbon atoms.

When used herein, the terms "cycloalkyl" and "cycloalkenyl" refer to groups having from three to eight ring carbon atoms.

When substituted, an alkyl, alkenyl, cycloalkyl or cycloalkenyl group may comprise up to four substituents, preferably up to two substituents. Suitable substituents for alkyl, alkenyl, cycloalkyl or cycloalkenyl groups include aryl, heteroaryl, heterocyclyl, ($C_{1-6}$)alkoxy, ($C_{1-6}$)alkylthio, aryl($C_{1-6}$)alkoxy, aryl($C_{1-6}$)alkylthio, amino, mono- or di-($C_{1-6}$)alkylamino, cycloalkyl, cycloalkenyl, carboxy and esters thereof, amide, ureido, guanidino, ($C_{1-6}$) alkylguanidino, amidino, ($C_{1-6}$)alkylamidino, ($C_{1-6}$)acyloxy, azido, hydroxy, and halogen.

When used herein the terms "heterocyclyl" and "heterocyclic" refer to, unless otherwise defined, non-aromatic, single and fused, rings suitably containing up to four heteroatoms in each ring, each of which is selected from oxygen, nitrogen and sulphur. Each heterocyclic ring preferably has from 4 to 7, preferably 5 or 6, ring atoms. A fused heterocyclic ring system may include carbocyclic rings and need include only one heterocyclic ring.

When substituted, a heterocyclyl group may comprise up to three substituents. Preferably a substituent for a heterocyclyl group is selected from oxo, and the group hereinbefore defined as suitable aryl substituents.

When used herein, the term "heteroaryl" suitably includes, unless otherwise defined, a mono- or bicyclic heteroaromatic ring system comprising up to four, preferably 1 or 2, heteroatoms each selected from oxygen, nitrogen and sulphur. Each ring may have from 4 to 7, preferably 5 or 6, ring atoms. A bicyclic heteroaromatic ring system may include a carbocyclic ring.

When substituted, a heteroaryl group may comprise up to three substituents. Preferably a substituent for a heteroaryl group is selected from the group hereinbefore defined as suitable aryl substituents.

Depending on the substituents, two or more diastereoisomers may be possible. In that situation the present invention includes the individual diastereoisomers and mixtures thereof.

The 2-hydroxy-substituted compounds of formula (I) are of the 2-(S) configuration.

Preferred compounds of the invention include:

6-Amino-3-pyridinylcarbonylcarbamic acid 2-(S)-hydroxymutilin 14-ester;

2-Amino-5-pyrimidinylcarbonylcarbamic acid 2-(S)-hydroxymutilin 14-ester;

2-Amino-5-thiazolylcarbonylcarbamic acid 2-(S)-hydroxymutilin 14-ester; and

2-Amino-4-thiazolylcarbonylcarbamic acid 2-(S)-hydroxymutilin 14-ester.

Further preferred compounds include:

3-Amino-6-pyridazinylcarbonylcarbamic acid 2-(S)-hydroxymutilin 14-ester;

(2,6-Diamino-4-pyrimidinylcarbonyl)carbamic acid 2-(S)-hydroxymutilin 14-ester, (5-Amino-6-methoxy-3-pyridinylcarbonyl)carbamic acid 2-(S)-hydroxymutilin 14-ester;

(5-Amino-6-methoxy-3-pyridinylcarbonyl)carbamic acid 19,20-dihydro-2-(S)-hydroxymutilin 14-ester, (6-Amino-3-pyridinylcarbonyl)carbamic acid 19,20-dihydro 2-(S)-hydroxymutilin 14-ester;

[2-(1-Piperazinyl)-5-pyrimidinylcarbonyl]carbamic acid 2-(S)-hydroxymutilin 14-ester;

(2-Methylamino-5-pyrimidinylcarbonyl)carbamic acid 19,20-dihydro-2-(S)-hydroxymutilin 14-ester;

(6-Amino-5-methoxy-3-pyridinylcarbonyl)carbamic acid 2-(S)-hydroxymutilin 14-ester;

(6-Dimethylamino-3-pyridinylcarbonyl)carbamic acid 2-(S)-hydroxymutilin 14-ester; and (6-Methylamino-3-pyridinylcarbonyl)carbamic acid 2-(S)-hydroxymutilin 14-ester.

Particularly preferred compounds include:

(5-Amino-6-methoxy-3-pyridinylcarbonyl)carbamic acid 2-(S)-hydroxymutilin 14-ester;

(5-Amino-6-methoxy-3-pyridinylcarbonyl)carbamic acid 19,20-dihydro-2-(S)-hydroxymutilin 14-ester;

(6-Amino-3-pyridinylcarbonyl)carbamic acid 19,20-dihydro-2-(S)-hydroxymutilin 14-ester;

(6-Dimethylamino-3-pyridinylcarbonyl)carbamic acid 2-(S)-hydroxymutilin 14-ester; and (3-Amino-6-pyridazinylcarbonyl)carbamic acid 2-(S)-hydroxymutilin 14-ester.

The compounds of this invention may be in crystalline or non-crystalline form, and, if crystalline, may optionally be hydrated or solvated. This invention includes within its scope stoichiometric hydrates as well as compounds containing variable amounts of water.

The compounds according to the invention are suitably provided in substantially pure form, for example at least 50% pure, suitable at least 60% pure, advantageously at least 75% pure, preferably at least 85% pure, more preferably at least 95% pure, especially at least 98% pure, all percentages being calculated as weight/weight.

Compounds of the invention that contain a basic group such as an amino substituent may be in the form of a free base or an acid addition salt. Compounds having an acidic group such as a carboxy substituent may be in the form of a pharmaceutically acceptable salt. Compounds of the invention having both a basic and an acidic centre may be in the form of zwitterions, acid addition salt of the basic centre or alkali metal salts (of the carboxy group). Pharmaceutically acceptable salts are preferred.

Pharmaceutically acceptable acid-addition salts include those described by Berge, Bighley, and Monkhouse, *J. Pharm. Sci.*, 1977, 66, 1–19. Suitable salts include the hydrochloride, maleate, and methanesulphonate; particularly the hydrochloride.

Pharmaceutically acceptable salts include those described by Berge, Bighley, and Monkhouse, *J. Pharm. Sci.*, 1977, 66, 1–19. Suitable salts include alkali metal salts such as the sodium and potassium salts.

In a further aspect the present invention provides a process for preparing compounds of formula (I), which process comprises reacting a compound of formula (II):

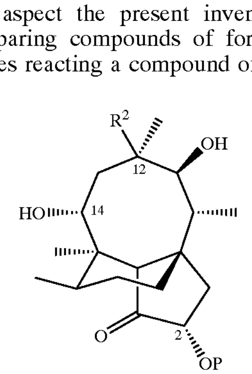

in which X and P are hydrogen or a hydroxyl protecting group, such as an acyl group, and $R^2$ is as hereinbefore defined;

with an acyl isocyanate of formula $R^{1A}CONCO$ in which $R^{1A}$ is $R^1$ as hereinbefore defined or a group convertible into $R^1$, for instance a group comprising a protected substituent therein and thereafter and if necessary:

(a) deprotecting a group X and/or P to generate hydroxyl groups at position 11 and 2, respectively, (b) converting a group $R^{1A}$ to $R^1$, for instance removing a protecting group, (c) converting a group $R^1$ to another group $R^1$, and (d) hydrogenating the vinyl group at position 12 to form an ethyl group.

Preferably, it is desirable to use a compound of formula (HI) in which both P and X are hydroxyl protecting groups.

Similar such processes have been previously described in WO 97/25309 and WO 98/05659 (SmithKline Beecham).

Methods for preparing acyl isocyanates are described in the literature. For example, they may be prepared by reaction of an acid chloride ($R^{1A}COCl$) with silver cyanate (e.g. as described by Murdock and Angier in *J. Org. Chem.*, 1962, 27, 3317), tri-n-butyl tin isocyanate (e.g. as described by Akteries and Jochims, *Chem. Ber.*, 1986, 119, 83), or trimethylsilyl isocyanate (e.g. as described by Sheludyakov et al., *J. Gen. Chem. USSR*, 1977, 2061–2067) in an inert solvent such as benzene, toluene, chloroform, dichloromethane, or 1,2-dichloroethane. Alternatively, they may be prepared by treating a primary amide ($R^{1A}CONH_2$) or N,N-bis(trimethylsilyl) derivative thereof, with oxalyl chloride or phosgene in an inert solvent (e.g. Speziale and Smith, *J. Org. Chem.*, 1962, 27, 3742; Kozyukov, et al., *Zh Obshch Khim*, 1983, 53, 2155).

The formation and reaction of the acyl isocyanate may be conveniently carried out in one process. This typically involves reaction of a compound of formula (II) with an acid chloride $R^{1A}COCl$ in the presence of silver cyanate and a tertiary base (e.g. triethylamine, diisopropyl ethylamine, pyridine), usually triethylamine, in an inert solvent (e.g. chloroform, dichloromethane, 1,2-dichloroethane).

Thus, in a further aspect the present invention provides a process for the preparation of a compound of formula (I) which process comprises reacting a compound of formula (II) with an acyl chloride compound of formula $R^{1A}COCl$, in the presence of silver cyanate and a base, such as triethylamine, and, thereafter, if necessary, carrying out one or more of the following steps in any desired order:

(e) deprotecting a group P and/or X to generate hydroxyl groups at position 2 and 11, respectively, (f) converting a group $R^{1A}$ to $R^1$, for instance removing a protecting group, (g) converting one group $R^1$ to another group $R^1$, and (h) hydrogenating the vinyl group at position 12 to form an ethyl group.

Preferably, it is desirable to use a compound of formula (II) in which both P and X are hydroxyl protecting groups.

Suitable hydroxy protecting groups are those well known in the art and which may be removed under conventional conditions and without disrupting the remainder of the molecule. A comprehensive discussion of the ways in which hydroxy groups may be protected and methods for cleaving the resulting protected derivatives is given in for example "Protective Groups in Organic Chemistry" (T. W. Greene and P. G. M. Wuts, Wiley-Interscience, New York, 2nd edition, 1991). Particularly suitable hydroxy protecting groups include, for example, triorganosilyl groups such as, for instance, trialkylsilyl and also organocarbonyl and organooxycarbonyl groups such as, for instance, acetyl, allyloxycarbonyl, 4-methoxybenzyloxycarbonyl and 4-nitrobenzyloxycarbonyl.

Representative values for P include acetate, dichloroacetate or trifluoroacetate, preferably dichloroacetate. Representative values for X include acetate, dichloroacetate or trifluoroacetate, preferably trifluoroacetate. After formation of the 14-O-carbamoyl derivative, the 2- and 11-O-acyl groups may be removed by selective hydrolysis (e.g. using NaOH in MeOH).

Protecting groups which can be used for substituents in $R^{1A}$, for instance amino, carboxy, hydroxy are well known in the art, see for instance "Protective Groups in Organic Chemistry" (T. W. Greene and P. G. M. Wuts, Wiley-Interscience, New York, 2nd edition, 1991). Particularly suitable hydroxy protecting groups include, for example, triorganosilyl groups such as, for instance, trialkylsilyl and also organocarbonyl and organooxycarbonyl groups such as, for instance, acetyl, allyloxycarbonyl, 4-methoxybenzyloxycarbonyl and 4-nitrobenzyloxycarbonyl. Particularly suitable carboxy protecting groups include alkyl and aryl groups, for instance methyl, ethyl and phenyl. Particularly suitable amino protecting groups include alkoxycarbonyl, 4-methoxybenzyloxycarbonyl and 4-nitrobenzyloxycarbonyl.

Compounds of formula (I) in which $R^1$=Et may be prepared by reducing a vinyl group $R^1$ by hydrogenation over a palladium catalyst (e.g. 10% Palladium-on-carbon) in a solvent such as ethyl acetate, ethanol, dioxane, or tetrahydrofuran, either before or after the carbamoylation of a compound of formula (II).

Compounds of formula (II) in which P and X are both hydroxyl protecting groups are novel intermediates which are of use in preparing compounds of formula (I).

Accordingly, in a further aspect, the present invention provides for a compound of formula (II) in which P and X are hydroxyl protecting groups, in particular an organocarbonyl group, for instance a $(C_{1-6})$alkylcarbonyl group in which the alkyl moiety may be substituted by from 1 to 3 halogen atoms, for instance trifluoroacetyl and dichloroacetyl. Preferably, P is dichloroacetyl and X is trifluoroacetyl. A preferred compound of formula (II) is:

(2S)-2-Dichloroacetoxy-11-O-trifluoroacetyl-mutilin.

A compound of formula (II) may be prepared from mutilin, via an intermediate 2-diazo compound, the preparation of which is similar to that described by H Berner, et al. in *Monatshefte fur Chemie*, 1981, vol. 112, pp 1441–1450. This intermediate may then be reacted with a carboxylic acid to give a 2-acyloxy-mutilin derivative. Typically, reaction with dichloroacetic acid gives a 2-dichloroacetoxy-mutilin derivative.

A preferred synthetic route for compounds of formula (I) is outlined in the following scheme:

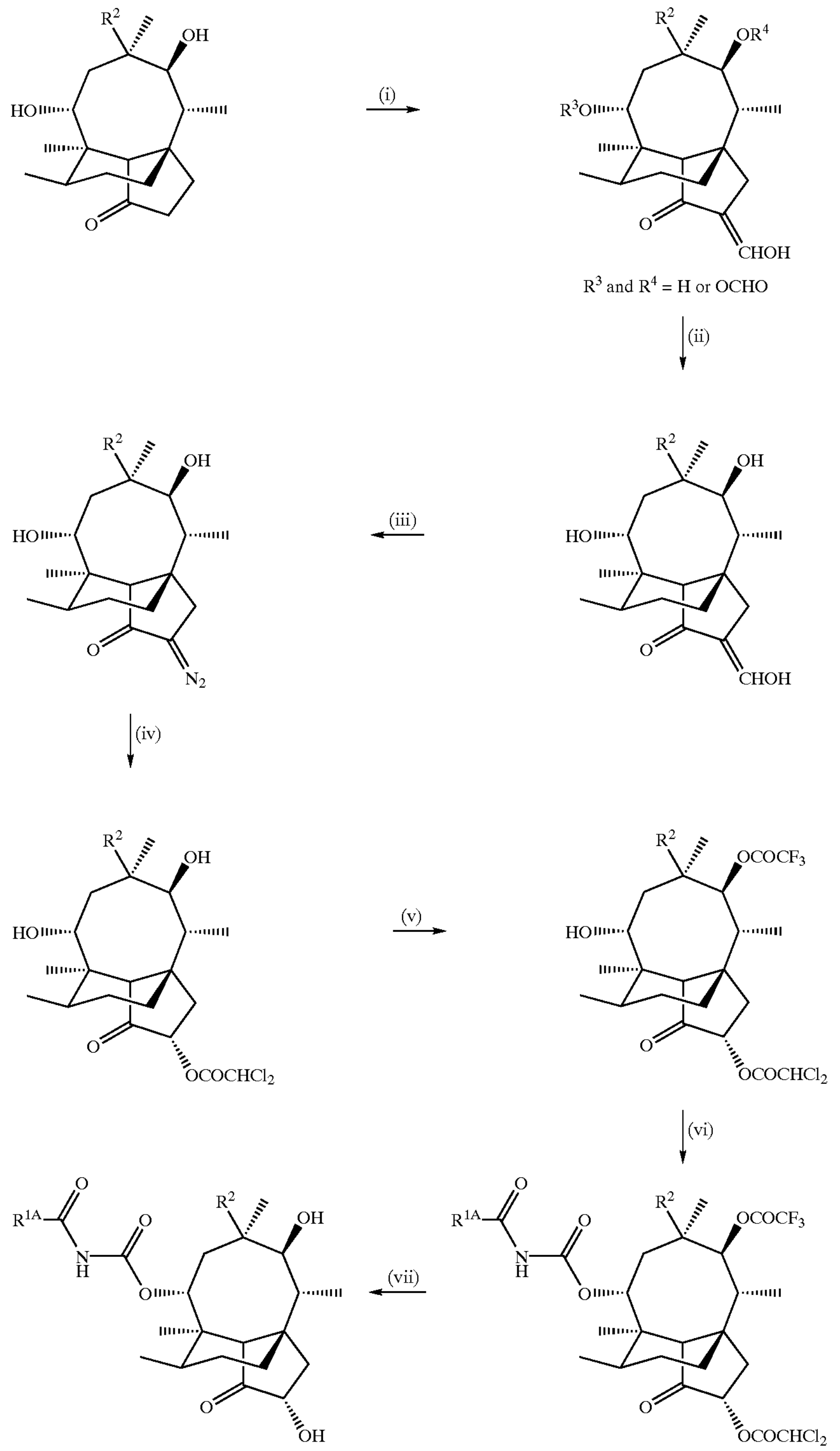

using the following reagents and conditions:
(i) ethyl formate, sodium methoxide, toluene, room temperature;
(ii) KOH/EtOH, room temperature;
(iii) tosyl azide, triethylamine, dichloromethane, −10° C. to room temperature;
(iv) dichloroacetic acid, dichloromethane, 0° C. to room temperature;
(v) trifluoroacetyl imidazole, tetrahydrofuran, room temperature;
(vi) $R^{1A}COCl$, silver cyanate, triethylamine, dichloromethane, room temperature;
(vii) 0.5M KOH, EtOH, room temperature.

The compounds of the present invention may contain a chiral centre, and therefore the above processes may produce a mixture of diastereoisomers. A single diastereoisomer may be prepared by separating such a mixture of diastereoisomers by conventional techniques such as chromatography or fractional crystallisation.

The compounds of this invention may be in crystalline or non-crystalline form, and, if crystalline, may optionally be hydrated or solvated. When some of the compounds of this invention are allowed to crystallise or are recrystallised from organic solvents, solvent of crystallisation may be present in the crystalline product. Similarly, some of the compounds of this invention may be crystallised or recrystallised from solvents containing water. In such cases water of hydration may be present in the crystalline product. Crystallisation procedures will usually produce stoichiometric hydrates. Compounds containing variable amounts of water may be produced by processes such as lyophilisation.

The compounds according to the invention are suitably provided in substantially pure form, for example at least 50% pure, suitable at least 60% pure, advantageously at least 75% pure, preferably at least 85% pure, more preferably at least 95% pure, especially at least 98% pure, all percentages being calculated as weight/weight. An impure or less pure form of a compound according to the invention may, for example, be used in the preparation of a more pure form of the same compound or of a related compound (for example a corresponding derivative) suitable for pharmaceutical use.

The present invention also includes pharmaceutically acceptable salts and derivatives of the compounds of the invention. Salt formation may be possible when one of the substituents carries an acidic or basic group. Salts may be prepared by salt exchange in conventional manner.

Acid-addition salts may be pharmaceutically acceptable or non-pharmaceutically acceptable. In the latter case, such salts may be useful for isolation and purification of the compound of the invention, or intermediates thereto, and will subsequently be converted into a pharmaceutically acceptable salt or the free base.

The compounds of the present invention and their pharmaceutically acceptable salts or derivatives have antimicrobial properties and are therefore of use in therapy, in particular for treating microbial infections in animals, especially mammals, including humans, in particular humans and domesticated animals (including farm animals). The compounds may be used for the treatment of infections caused by, for example, Gram-positive and Gram-negative bacteria and mycoplasmas, including, for example, *Staphylococcus aureus, Staphylococcus epidermidis, Enterococcus faecalis, Streptococcus pyogenes, Streptococcus agalactiae, Streptococcus pneumoniae, Haemophilus* sp., *Neisseria* sp., *Legionella* sp., *Chlamydia* sp., *Moraxella catarrhalis, Mycoplasma pneumoniae*, and *Mycoplasma gallisepticum.*

The present invention also provides a method of treating microbial infections in animals, especially in humans and in domesticated mammals, which comprises administering a compound of the invention or a pharmaceutically acceptable salt or derivative or solvate thereof, or a composition according to the invention, to a patient in need thereof.

Compounds of the present invention show good activity against *Chlamydia pneumoniae*. This has been implicated in heart disease, in particular in promoting vascular infection (see for instance FR 2 771 008-A1, Hoechst Marion Roussel SA). Accordingly, in a further aspect, the present invention provides a method of preventing *C. pneumoniae*-induced atherosclerosis which method comprises treating a subject in need thereof with an effective amount of a compound of formula (I). A compound of formula (I) may also be used in combination with an anti-atherosclerotic agent, to reduce the incidence of heart attack and other cardiac events. Representative examples of anti-atherosclerotic agents include the class of cholesterol-lowering compounds referred to generically as "statins", for instance atorvastatin (Lipitor, Warner Lambert), pravastatin (Pravachol), simvastatin (Lipovas, Merck) and cerivastatin (Baycol, Bayer). It has also been suggested that *Chlamydia pneumoniae* may contribute to Alzheimer's Disease. Accordingly, in a further aspect, the present invention provides a method of treating Alzheimer's Disease which method comprises treating a subject in need thereof with an effective amount of a compound of formula (I).

The invention further provides the use of a compound of the invention or a pharmaceutically acceptable salt or derivative or solvate thereof in the preparation of a medicament for use in the treatment of microbial infections.

Compounds of the present invention may be used to treat skin and soft tissue infections and acne, by topical application. Accordingly, in a further aspect the present invention provides the use of a compound of the invention or a pharmaceutically acceptable salt or derivative or solvate thereof in the preparation of a medicament adapted for topical administration for use in the treatment of skin and soft tissue infections and also in the treatment of acne in humans.

Compounds of the present invention may be also used for the elimination or reduction of nasal carriage of pathogenic bacteria such as *S. aureus, H. influenzae, S. pneumonia* and *M. catarrhalis*, in particular colonisation of the nasospharynx by such organisms, by the administration of a compound of the present invention thereto. Accordingly, in a further aspect, the present invention provides for the use of a compound of the invention or a pharmaceutically acceptable salt or derivative or solvate thereof in the manufacture of a medicament adapted for administration to the nasal cavity, for reducing or eliminating the nasal carriage of pathogenic organisms. Preferably, the medicament is adapted for focussed delivery to the nasopharynx, in particular the anterior nasopharynx.

Such reduction or elimination of nasal carriage is believed to be useful in prophylaxis of recurrent acute bacterial sinusitis (RABS) or recurrent otitis media in humans, in particular in reducing the number of episodes experienced by a patient over a given period of time or increasing the time intervals between episodes. Accordingly, in a further aspect, the present invention provides for the use of a compound of the invention or a pharmaceutically acceptable salt or derivative or solvate thereof in the manufacture of a medicament adapted for administration to the nasal cavity, for prophylaxis of recurrent acute bacterial sinusitis or recurrent otitis media.

The compounds according to the invention may suitably be administered to the patient at a daily dosage of from 1.0 to 50 mg/kg of body weight. For an adult human (of approximately 70 kg body weight), from 50 to 3000 mg, for example about 1500 mg, of a compound according to the invention may be administered daily. Suitably, the dosage for adult humans is from 5 to 20 mg/kg per day. Higher or lower dosages may, however, be used in accordance with normal clinical practice.

To lessen the risk of encouraging the development of resistant organisms during prophylaxis of recurrent otitis media or recurrent acute bacterial sinusitis, it is preferred to administer the drug on an intermittent, rather than a continual, basis. In a suitable intermittent treatment regimen for prophylaxis of recurrent otitis media or recurrent sinusitis, drug substance is administered on a daily basis, for a small number of days, for instance from 2 to 10, suitably 3 to 8, more suitably about 5 days, the administration then being repeated after an interval, for instance, on a monthly basis over a period of months, for instance up to six months. Less preferably, the drug substance may be administered on a continuing, daily basis, over a prolonged period, for instance several months. Suitably, for prophylaxis of recurrent otitis media or recurrent sinusitis, drug substance is administered once or twice a day. Suitably, drug substance is administered during the winter months when bacterial infections such as recurrent otitis media and recurrent sinusitis tend to be more prevalent. The drug substance may be administered at a dosage of from 0.05 to 1.00 mg, typically about 0.1 to 0.2 mg, in each nostril, once or twice a day.

More generally, the compounds and compositions according to the invention may be formulated for administration in any convenient way for use in human or veterinary medicine, by analogy with other antibiotics.

Accordingly, in a further aspect, the present invention provides a pharmaceutical composition comprising a compound of the invention or a pharmaceutically acceptable salt or derivative or solvate thereof together with a pharmaceutically acceptable carrier or excipient.

The compounds and compositions according to the invention may be formulated for administration by any route, for example oral, topical or parenteral. The compositions may, for example, be made up in the form of tablets, capsules, powders, granules, lozenges, creams, syrups, sprays or liquid preparations, for example solutions or suspensions, which may be formulated for oral use or in sterile form for parenteral administration by injection or infusion.

Tablets and capsules for oral administration may be in unit dosage form, and may contain conventional excipients including, for example, binding agents, for example, syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate or acacia; non-aqueous vehicles (which may include edible oils), for example almond oil, oily esters (for example glycerine), propylene glycol, or ethyl alcohol; preservatives, for example methyl or propyl p-hydroxybenzoate or sorbic acid; and, if desired, conventional flavouring and colour agents.

Compositions according to the invention intended for topical administration may, for example, be in the form of ointments, creams, lotions, eye ointments, eye drops, ear drops, nose drops, nasal sprays, impregnated dressings, and aerosols, and may contain appropriate conventional additives, including, for example, preservatives, solvents to assist drug penetration, and emollients in ointments and creams. Such topical formulations may also contain compatible conventional carriers, for example cream or ointment bases, ethanol or oleyl alcohol for lotions and aqueous bases for sprays. Such carriers may constitute from about 1% to about 98% by weight of the formulation; more usually they will constitute up to about 80% by weight of the formulation.

Compositions according to the invention intended for topical administration, in addition to the above, may also contain a steroidal anti-inflammatory agent; for example, betamethasone.

Compositions according to the invention may be formulated as suppositories, which may contain conventional suppository bases, for example cocoa-butter or other glycerides.

Compositions according to the invention intended for parenteral administration may conveniently be in fluid unit dosage forms, which may be prepared utilizing the compound and a sterile vehicle, water being preferred. The compound, depending on the vehicle and concentration used, may be either suspended or dissolved in the vehicle. In preparing solutions, the compound may be dissolved in water for injection and filter-sterilised before being filled into a suitable vial or ampoule, which is then sealed. Advantageously, conventional additives including, for example, local anaesthetics, preservatives, and buffering agents can be dissolved in the vehicle. In order to enhance the stability of the solution, the composition may be frozen after being filled into the vial, and the water removed under vacuum; the resulting dry lyophilised powder may then be sealed in the vial and a accompanying vial of water for injection may be supplied to reconstitute the liquid prior to use. Parenteral suspensions may be prepared in substantially the same manner except that the compound is suspended in the vehicle instead of being dissolved and sterilisation cannot be accomplished by filtration. The compound may instead be sterilised by exposure to ethylene oxide before being suspended in the sterile vehicle. Advantageously, a surfactant or wetting agent is included in such suspensions in order to facilitate uniform distribution of the compound.

A compound or composition according to the invention is suitably administered to the patient in an antimicrobially effective amount.

A composition according to the invention may suitably contain from 0.001% by weight, preferably (for other than spray compositions) from 10 to 60% by weight, of a compound according to the invention (based on the total weight of the composition), depending on the method of administration.

When the compositions according to the invention are presented in unit dosage form, for instance as a tablet, each unit dose may suitably comprise from 25 to 1000 mg, preferable from 50 to 500 mg, of a compound according to the invention.

Representative compositions of the present invention include those adapted for intranasal administration, in particular, those that will reach into the nasopharynx. Such compositions are preferably adapted for focussed delivery to, and residence within, the nasopharynx. The term 'focussed delivery' is used to mean that the composition is delivered to the nasopharynx, rather than remaining within the nares. The term 'residence' within the nasopharynx is used to mean that the composition, once delivered to the nasopharynx, remains within the nasopharynx over a course of several hours, rather than being washed away more or less immediately. Preferred compositions include spray compositions and creams. Representative spray compositions include aqueous compositions, as well as oily compositions that contain amphiphilic agents so that the composition increases in viscosity when in contact with moisture. Creams may also be used, especially creams having a rheology that allows the cream to spread readily in the nasopharynx.

Preferred aqueous spray compositions include, in addition to water, further excipients including a tonicity modifier such as a salt, for instance sodium chloride; preservative, such as benzalkonium salt; a surfactant such as a non-ionic surfactant, for instance a polysorbate; and buffer, such as sodium dihydrogen phosphate; present in low levels, typically less than 1%.

The pH of the composition may also be adjusted, for optimum stability of the drug substance during storage. For compounds of the present invention, a pH in the range 5 to 6, preferably about 5.3 to 5.8, typically about 5.5 is optimal.

Representative oily spray and cream compositions are described in WO 99/07341 and WO 99/12520 (SmithKline Beecham). Representative aqueous sprays have previously been described in WO 99/21855 (SmithKline Beecham).

Suitably, the drug substance is present in compositions for nasal delivery in between 0.001 and 5%, preferably 0.005 and 3%, by weight of the composition. Suitable amounts include 0.5% and 1% by weight of the composition (for oily compositions and creams) and from 0.01 to 0.2% (aqueous compositions).

Spray compositions according to the present invention may be delivered to the nasal cavity by spray devices well known in the art for nasal sprays, for instance an air lift pump. Preferred devices include those that are metered to provide a unit volume of composition, preferably about 100 μl, and optionally adapted for nasal administration by addition of a modified nozzle.

The invention is illustrated by the following Examples.

Note on Naming of Pleuromutilin Analogues

The compound of formula (a) has, under the IUPAC system, the systematic name (1S, 2R, 3S, 4S, 6R, 7R, 8R, 14R)-3,6-dihydroxy-2,4,7,14-tetramethyl4-vinyl-tricyclo $[5.4.3.0^{1,8}]$tetradecan-9-one. It is also referred to using the trivial name mutilin and with the numbering system described by H. Bemer, G. Schulz, and H. Schneider in *Tetrahedron,* 1981, 37, 915–919.

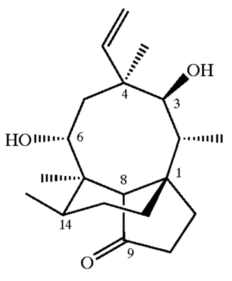

(a) IUPAC numbering

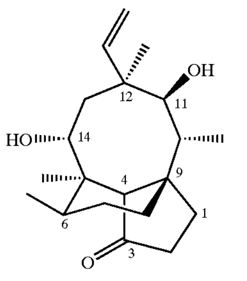

(a) Mutilin numbering

Preparation 1

(2S)-2-Dichloroacetoxy-11-O-trifluoroacetyl-mutilin

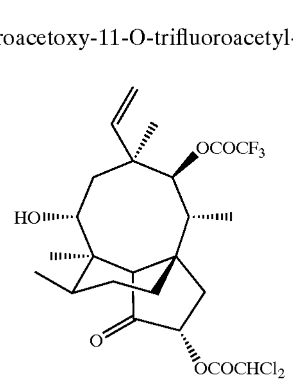

(a) Formylated Derivatives of Mutilin

The reaction was carried out similarly to that described by A. J. Birch, C. W. Holzapfel and R. W. Rickards (Tet (Suppl) 1996 8 part III 359). Mutilin (6 g) in toluene (330 ml) and methyl formate (100 ml) was treated with sodium methoxide (3 g) and stirred under argon for 8 hours. Ice-water (100 ml) was added, followed by 2N HCl (220 ml). The mixture was shaken and separated and the aqueous extracted with ether. The combined organic was dried and evaporated and the residue chromatographed, eluting with ethyl acetate/hexane mixtures. First eluted was 2-hydroxymethylenemutilin 11,14-diformate (2.33 g): $^1$HNMR ($CDCl_3$) inter alia 5.02 (1H, d), 5.77 (1H, d), 6.94 (1H, s), 7.89 (1H, s), 8.10 (1H, s). Second to be eluted was 2-hydroxymethylenemutilin 11-formate (3.0 g): $^1$H NMR ($CDCl_3$) inter alia 4.40 (1H, d), 5.11 (1H, d), 7.06 (1H, s), 8.25 (1H, d, J O.8 Hz). Third to be eluted was a mixture (2:1) of 2-hydroxymethylenemutilin 14-formate and 2-hydroxymethylenemutilin (1.8 g).

(b) 2-Hydroxymethylenemutilin

A mixture of 2-hydroxymethylenemutilin 11,14-diformate (2.33 g) and [2-hydroxymethylenemutilin 14-formate+2-hydroxymethylene mutilin] (1.8 g) was dissolved in ethanol (30 ml) and treated with 0.5M KOH in ethanol (60 ml). After 1 hour the solution was diluted with ethyl acetate (200 ml), washed with 2M HCl (120 ml) and water (100 ml), dried and evaporated to provide 2-hydroxymethylenemutilin as a foam (3.6 g); $^1$H NMR ($CDCl_3$) inter alia 3.45 (1H, d), 4.37 (1H, d), 6.97 (1H, s).

(c) 2-Diazomutilin

A solution of 2-hydroxymethylenemutilin (3.6 g) in dichloromethane was cooled to −10° C. under argon, treated with triethylamine (4.6 ml) and tosyl azide (3.55 g) and warmed to room temperature. After 6 hours the solution was washed with 0.5M HCl(150 ml) and water (100 ml), dried and evaporated. The 2-diazomutilin was obtained as yellow crystals (1.7 g) from ethyl acetate/hexane; IR ($CHCl_3$) 3634, 2082 and 1670 $cm^{-1}$.

(d) (2S)-2-Dichloroacetoxymutilin

A solution of 2-diazomutilin (1.7 g) in dichloromethane (40 ml) was ice-cooled and treated dropwise with dichloracetic acid (0.5 ml). The bath was removed and after 30 minutes the solution was colourless. It was washed with aqueous $NaHCO_3$ (50 ml), dried and evaporated. Chromatography, eluting with 1:3 ethyl acetate/hexane, gave the title compound as the less polar of 2 major products (white foam, 1.6 g): $^1$H NMR ($CDCl_3$) inter alia 3.33 (1H, t, J 5.8 Hz), 4.33 (1H, d, J 7 Hz), 5.04 (1H, t, J 9 Hz), 5.2–5.4 (2H, m), 5.96 (1H, s), 6.14 (1H, dd, J 17.5 and 10.5 Hz).

(e) (2S)-2-Dichloroacetoxy-11-O-trifluoroacetylmutilin (2S)-2-Dichloroacetoxymutilin (5.8 g, 0.012 mole) in dry tetrahydrofuran (120 ml) was treated with trifluoroacetylimidazole (1.54 ml, 0.0135 mole) and stirred at ambient temperature for 18 hours. Ethyl acetate (200 ml) was added to the mixture which was then washed with dilute sodium chloride solution (2×200 ml). The organic layer was separated, dried ($Na_2SO_4$), filtered and evaporated to dryness. Chromatography on silica gel, eluting with ethyl acetate/hexane (9:1) gave the title compound (4.98 g, 71%); $^1$H NMR ($CDCl_3$) inter alia 0.85 (3H, d, J 7 Hz), 0.95 (3H, d, J 7 Hz), 1.05 (3H, s), 1.39 (3H, s), 4.29 (1H, t, J 7 Hz), 4.86 (1H, d, J 7 Hz), 5.08 (1H, t, J 9 (1H, s).

Preparation 2

6-tert-Butyloxycarbonylaminonicotinic Acid

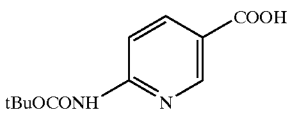

Methyl 6-aminonicotinate (10 g) in t-butanol (500 ml) was treated with di-tert-butyldicarbonate (15.8 g) and heated at 100° C. for 36 hours. The mixture was concentrated in-vacuo. Trituration with diethyl ether gave methyl 6-tert-butyloxycarbonylaminonicotinate (12.8 g). Treatment of this compound with lithium hydroxide monohydrate in a mixture of tetrahydrofuiran (150 ml) and water (150 ml) for 18 hours and evaporating to a small volume was followed by acidification with citric acid. Filtration gave the title compound as a white solid (8.99 g, 57%). M.S.(−ve ion chemical ionisation)m/z 237([M-H]$^-$, 80%),193 (100%).

Preparation 3

6-tert-Butyloxycarbonylaminoisonicotinic Acid

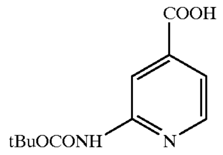

The title compound was prepared analogously to Preparation 2 from methyl 6-aminoisonicotinate (D. J. Stanonis, J. Org. Chem. 22 (1957)475) to give 1.54 g. M.S.(−ve ion chemical ionisation)m/z 237([M-H]$^-$, 55%), 193 (100%).

Preparation 4

Sodium 5-bis-t-butoxyearbonylaminopyridin-3-ylcarboxylate (a) Ethyl 5-aminonicotinate 5-Aminonicotinic acid (2.2 g) (Bachman and Micucci, J. Amer. Chem. Soc. 70 (1948) 2381) in ethanol (20 ml) was ice-cooled, saturated with HCl gas and refluxed 4 hours. The mixture was concentrated to low volume and partitioned between EtOAc (100 ml) and saturated $NaHCO_3$ solution (100 ml). The organic phase was washed with further aqueous $NaHCO_3$, dried and evaporated to leave the title compound as a white solid (1.34 g). M.S. (+ve ion chemical ionisation) m/z 167 (MH$^+$,100%).

(b) Ethyl 5-bis-t-butoxycarbonylaminopyridin-3-yl Carboxylate

A solution of ethyl 5-aminonicotinate (1.3 g) in 1,2-dichloroethane (20 ml) was treated with triethylamine (2.4 ml), di-t-butyldicarbonate (5.12 g) and 4-dimethylaminopyridine (14 mg) and refluxed 1 hour. The solvent was evaporated and the residue taken up in EtOAc (50 ml), washed with water (2×50 ml), dried and evaporated. Chromatography gave the title compound as a white solid (947 mg). M.S. (+ve ion chemical ionisation) m/z 367(MH$^+$, 40%), 167(100%).

(c) Sodium 5-bis-t-butoxycarbonylaminopyridin-3-ylcarboxylate

A solution of ethyl 5-bis-t-butoxycarbonylaminopyridin-3-ylcarboxylate (0.9 g) in dioxan (15 ml)/water (1 ml) was treated with 2N aqueous NaOH (1.62 ml) and stirred overnight. The solution was evaporated to give the title compound as a solid, which was dried under vacuum (0.912 g). M.S. (+ve ion chemical ionisation) m/z 339(MH$^+$ free acid, 3%),167(100%).

Preparation 5

Sodium 6-bis-t-butoxycarbonylaminopyridin-2-ylcarboxylate

The title compound was prepared analogously to Preparation 4, steps 2 and 3 from ethyl 6-aminopyridin-2 ylcarboxylate (Ferrari and Marcon, Farmaco Ed. Sci. 14 (1959) 594–596) in quantitative overall yield. NMR δ($CD_3OD$) 1.39(18H,s), 7.33(1H,dd), 7.76(1H,t), 7.95 (1H,dd).

Preparation 6

Sodium 5-bis-t-butoxycarbonylaminopyridin-2-ylcarboxylate

The title compound was prepared analogously to Preparation 4, steps 2 and 3 from methyl 5-aminopyridin-2-ylcarboxylate (O. P. Shkurko and V. P. Mamaev, Chem. Heterocycl. Compd. 26 (1990)47–52) in 52% overall yield. NMR δ($D_2O$) 1.35(18H,s), 7.77(1H,dd), 7.92(1H,d), 8.38 (1H,d).

Preparation 7

Sodium 4-bis-t-butoxycarbonylaminopyridin-2-ylcarboxylate (a) Methyl 4-aminopyridin-2-ylcarboxylate A solution of methyl 4-nitropyridin-2-ylcarboxylate (0.7 g) (Deady et. al., Aus. J. Chem. 24 (1971)385–390) in methanol (30 ml) was treated with 10% Pd/C (0.3 g) and stirred under hydrogen at atmospheric pressure overnight. The solution was filtered and evaporated to yield the title compound (0.55 g). NMR δ($CDCl_3$) 3.97(3H,s), 4.34(2H, broad), 6.65(1H,dd), 7.39(1H,d), 8.32(1H,d).

(b) and (c)

Were carried out analogously to steps (b) and (c) of preparation 4 to provide the title sodium salt in overall 67% yield. MS(−ve ion chemical ionisation) m/z 337 ([M-H]$^-$ free acid, 70%, 178(100%).

Preparation 8

Sodium 6-methoxynicotinate

Hydrolysis of methyl 6-methoxynicotinate in a manner analogous to step (c) of preparation 4 provided the title compound.

Preparation 9

2-t-butoxycarbonylaminothiazole-5-carboxylic Acid (a) Methyl 2-bis-t-butoxycarbonylaminothiazole-5-carboxylate A solution of methyl 2-aminothiazole-5-carboxylate (2.3 g) (R. Noto, M. Ciofalo, F. Buccheri, G. Werber and D. Spinelli, J C S Perkin Trans. 2, (1991)349–352) in dichloromethane (60 ml) was treated with triethylamine (2 ml), a catalytic amount of 4-dimethylaminopyridine and di-t-butyldicarbonate (8 g) and stirred overnight. The solution was evaporated to low volume, applied to a silica column and eluted with ethyl acetate/hexane to provide the title compound (3.56 g).

(b) 2-t-Butoxycarbonylaminothiazole-5-carboxylic Acid

A solution of methyl 2-bis-t-butoxycarbonylaminothiazole-5-carboxylate (3.56 g) in dioxan (50 ml) was treated with 2N NaOH solution (9 ml), stirred 1 hour, treated with a further 17 ml of 2N NaOH and stirred a further hour. The mixture was taken to pH 8 with 2N HCl and evaporated. The solid was taken up in water (10 ml), treated with a solution of citric acid (6.6 g) in water (20 ml) and extracted with ethyl acetate (30 ml). The ethyl acetate was separated, washed with water (3×20 ml), dried and evaporated to yield the title compound as a solid (0.96 g). NMR δ(DMSO) 1.50(9H,s), 7.95(1H,s), 11.90(1H, broad).

Preparation 10

2-t-Butoxycarbonylaminothiazole-4-carboxylic Acid (a) Ethyl 2-aminothiazole-4-carboxylate 2-Aminothiazole-4-carboxylic acid hydrobromide (10 g) (E. C. Roberts and Y. F. Shealy, J. Med. Chem. 15 (1972) 1310–1312) in ethanol (35 ml) was treated with conc. sulfuric acid and refluxed for 48 hours. The solution was evaporated to 25% of original volume and water (20 ml) added. It was made basic by addition of $NaHCO_3$, the solid filtered, washed with water and dried under vacuum to give the title compound (5.64 g). NMR δ($CDCl_3$) 137 (3H,t), 4.36(2H,q), 5.39(2H, broad), 7.43(1H,s).

(b) and (c)

Were carried out analogously to steps (b) and (c) of preparation 9 to provide the title acid. NMR ($CD_3OD$) 1.45 (9H,s), 7.77 (1H,s).

Preparation 11

Sodium 2,6-bis(bis-t-butoxycarbonylamino) pyrimidine-4-carboxylate

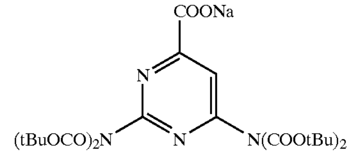

(a) Methyl 2,6-diaminopyrimidine-4-carboxylate 2,6-diamino pyrimidine-4-carboxylic acid (G. D. Davies, F. Baiocchi, R. K. Robins and C. C. Cheng, J. Org Chem 26 (1961) 2755–2759) was esterified with HCl/MeOH using the procedure of Preparation 4, step (a) in 100% yield. $^1$HNMR δ(DMSO) 3.90(3H,s), 6.72 (1H,s), 8.57 (broad), 8.93 (broad).

(b) was carried out analogously to step (a) of Preparation 9 and (c) analogously to step (c) of Preparation 4 to give the title compound (30% over 2 steps). $^1$HNMR δ(DMSO) 1.38(18H, s), 4.45(18H, s), 7.71 (1H,s).

Preparation 12 2-(1-t-butoxycarbonylpiperidin-4-yl) thiazole-4-carboxylic Acid

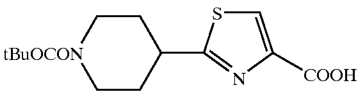

A solution of ethyl 2-(1-t-butoxycarbonylpiperidin-4-yl) thiazole-4-carboxylate (from Tripos UK Ltd) (340 mg) in dioxan (5 ml)/water (1 ml) was treated with 2N NaOH (0.6 ml) and left overnight. The solution was diluted with EtOAc (20 ml) and 1M citric acid solution (10 ml), shaken, separated. The organic was washed with water (3x10 ml), dried and evaporated to give the title compound as a solid (295 mg). MS (+ve ion electrospray) m/z 335 ($MNa^+$, 30%) 239 (100%);(−ve ion electrospray) m/z 267($[M-COOH]^-$, 100%).

Preparation 13

2-Methoxypyrimidine-5-carboxylic Acid

A solution of methyl 2-methoxypyrimidine-5-carboxylate (944 mg) (Z. Budesinsky and J. Vavrina, Collect. Czech. Chem. Commun. 37 (1972)1721–1733) in dioxan (33 ml)/water (33 ml) was treated with 2N NaOH (3.37 ml), left overnight and evaporated to low volume. The residue was taken up in water (30 ml), the pH adjusted to 2 by addition of 2N HCl and the mixture extracted with EtOAc (4×30 ml). The EtOAc was dried and evaporated to give the title compound as a white solid (605 mg) $^1$HNMR δ(DMSO) 4.00(3H,s), 9.03(2H,s).

Preparation 14

(2S)-2-Dichloroacetoxy-19,20-dihydro-11-O-trifluoroacetylmutilin

2-Diazo-19,20, dihydromutilin(H. Bemer, G. Schulz and G. Fischer, Monatsh. für Chemie, 112 (1981)1441–1450) was treated as in Preparation 1 steps (d) and (e) to provide the title compound. MS (−ve ion electrospray)m/z 603 ($MOAc^-$,65%), 543 ($[M-H]^-$,100%).

Preparation 15

Sodium 2-bis-t-butoxycarbonylaminopyrazine-5-carboxylate

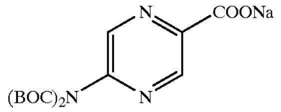

Ethyl 2-aminopyrazine-5-carboxylate (E. Felder, D. Pitre and E. B. Grabitz, Helv. Chim. Acta 47 (1964) 873–876) was treated analogously to step (b) of Preparation 9 and then step (c) of Preparation 4 to give the title compound as a white solid. NMR δ(DMSO) 1.38(18H,s), 8.51 (1H,s), 8.88(1H,s)

Preparation 16

Sodium 2-N-t-butoxycarbonyl-N-methylaminopyrimidine-5-carboxylate

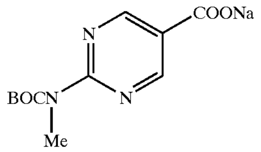

2-N-methylaminopyrimidine-5-carboxylic acid (D. J. Brown and M. N. Paddon-Row, J. Chem. Soc. C, (1966) 164–166) was esterified using the procedure of Preparation 4 (step (a). The ester was treated according to step (a) of Preparation 9 and then step (c) of Preparation 4 to give the title compound. NMR δ(DMSO) 1.42(9H,s), 3.28(3H,s) and 8.91(2H,s).

Preparation 17

Sodium 5-bis-t-butoxycarbonylamino-6-methoxynicotinate

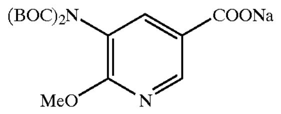

Methyl 5-amino-6-methoxynicotinate (Morisawa et. al., Agric.Biol.Chem. 40, (1976) 101) was treated according to step (a) of Preparation 9 and then step (c) of Preparation 4 to give the title compound. MS (−ve ion chemical ionisation) m/z 367 ($[M-H]^-$, 100%).

Preparation 18

Sodium 6-bis-t-butoxycarbonylamino-5-methoxynicotinate

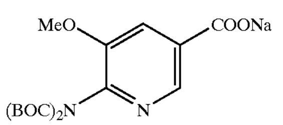

(a) Methyl 6-amino-5-methoxynicotinate

A mixture of 2-amino-5-bromo-3-methoxypyridine (7 g) (den Hertog et al, Recl.Trav.Chim.Pays-Bas, 74 (1955), 1171), bis(triphenylphosphine)palladium dibromide (3.5 g) and tri-n-butylamine (9 ml) in methanol (35 ml) was subjected to 80 psi pressure of carbon monoxide and heated at 112° C. for 16 hours. The mixture was cooled and evaporated and the residue chromatographed, eluting with 1:1 EtOAc/hexane to give the title compound (2.32 g). MS (+ve ion chemical ionisation) m/z 183 ($MH^+$, 100%).

(b) and (c) were carried out analogously to Preparation 9, step (a) and Preparation 4, step (c) to give sodium 6-bis-t-butoxycarbonylamino-5-methoxynicotinate (overall 77%). MS (−ve ion chemical ionisation) m/z 367 ($[M-H]^-$, 100%).

Preparation 19

Sodium 6-bis-t-butoxycarbonylamino-5-nitronicotinate

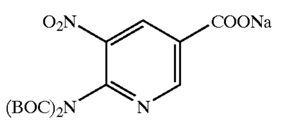

6-Amino-5-nitronicotinic acid (Marckwald, Chem.Ber. 27, (1894), 1336) was esterified by the procedure of Preparation 4, step (a), N-protected as described in Preparation 9, step (a) and the ester hydrolysed by the procedure of Preparation 4, step (c) to give the title compound. NMR δ(DMSO) 1.32(18H, s), 8.72(1H, s), 9.07(1H, s)

Preparation 20

Sodium 2-bis-t-butoxycarbonylamino-6-methoxypyrimidine-4-carboxylate

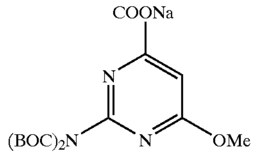

(a) Methyl 2-chloro-6-methoxypyrimidine-4-carboxylate

Methyl 2,6-dichloropyrimidine-4-carboxylate (10 g) (M. Winn et. al., J.Med.Chem. 36 (18), (1993), 2676–2688) in methanol (100 ml) was treated with sodium ethoxide (3 g) and left for 16 hours. Methanol was evaporated and the residue partitioned between dichloromethane and saturated aqueous $NaHCO_3$. The organic was washed with brine, dried and evaporated to give the title compound (24%). NMR δ($CDCl_3$) 4.00(3H, s), 4.07(3H, s), 7.37(1H, s).

(b) Sodium 2-chloro-6-methoxypyrimidine-4-carboxylate

Methyl ester (a) was hydrolysed according to preparation 4, step (c), to give title compound (100%). NMR δ(DMSO) 3.93(3H, s), 7.04(1H, s).

(c) Methyl 2-amino-6-methoxypyrimidine 4-carboxylate

A solution of sodium 2-chloro-6-methoxypyrimidine-4-carboxylate (2 g) in conc. aqueous ammonia (30 ml) was refluxed 4 hours and evaporated to dryness. The residue was taken up in methanol (200 ml) treated with conc. sulfuric acid (1 ml) and refluxed 16 hours. After evaporation to low volume, the mixture was partitioned between EtOAc and saturated aqueous $NaHCO_3$. The organic was washed with brine, dried and evaporated to give the title compound as a white solid (700 mg). NMR δ($CD_3OD$) 3.92(3H,s), 3.94 (3H,s), 6.81(1H,s).

(d) Sodium 2-bis-t-butoxycarbonylaminio-6-methoxypryimidine-4-carboxylate

Aminopyrimidine (c) was protected according to the procedure of Preparation 4, step (b) and the ester hydrolysed according to the procedure of Preparation 4, step (c) to give the title compound.

Preparation 21

Sodium 2-bis-t-butoxycarbonylaminopyrinmidin-4-ylcarboxylate

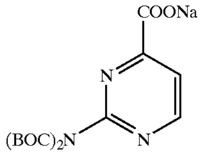

The title compound was prepared analogously to Preparation 4 from 2-aminopyrimidine-4-carboxylic acid (T. Matsukawa, K. Shirakawa, J. Pharm. Soc. Japan (1952), 72, 909–912). NMR δ(DMSO) 1.39(18H,s), 7.59(1H,d, J 5 Hz), 8.72 (1H, d, J 5 Hz)

Preparation 22

6-N-t-Butoxycarbonyl-N-methylaminonicotinic Acid

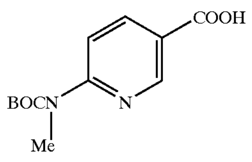

(a) 6-Methylaminonicotinic acid hydrochloride 6-chloronicotinic acid (4.5 g) was dissolved in methanol (50 ml), treated with 33% methylamine in ethanol solution (25 ml) and heated in a sealed bomb at 140° C. for 18 hours. The mixture was cooled and evaporated to dryness. Trituration with 1:1 methanol/diethyl ether gave the title compound (3.7 g, 69%). MS (+ve is an electrospray) m/z 153 ($MH^+$. 100%).

(b) Methyl (6-methylaminonicotinate

6-Methylaminonicotinic acid hydrochloride (3.65 g) in methanol (100 ml) was treated with conc. sulphuric acid (2 ml) and heated under reflux for 18 hours. The mixture was evaporated to dryness and the residue partitioned between ethyl acetate and saturated sodium bicarbonate solution. The organic layer was dried and evaporated to dryness to give the title compound (1.07 g) M.S(+ve ion electrospray) m/z 167 ($MH^+$, 100%).

(c) Methyl 6N-t-butoxycarbonyl-N-methylamino nicotinate

The title compound was prepared analogously to preparation 4, step (b) to give (1.41 g, 58%).

(d) 6-N-t-Butoxycarbonyl-N-methylaminonicotinic Acid

Ester hydrolysis was carried out analogously to the ester hydrolysis in Preparation 2 to give the title compound (76%). MS (−ve ion chemical ionisation) m/z 251 ($[M-H]^-$, 100%)

Preparation 23

Sodium 3-(N-t-butoxycarbonyl-N-methylamino) pyridazine-6-carboxylate

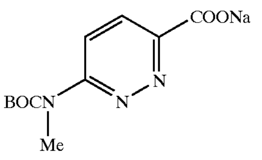

(a) 3-Methylaminopyridazine-carboxylic Acid

3-Chloropyridazine-6-carboxylic acid (2.5 g) (R. F. Homer, H. Gregory, W. G. Overend and L. F. Wiggins, J. Chem.Soc (1948) 2195–9) was treated with 8M methylamine in ethanol (2.16 ml) and heated at 100° C. in a sealed bomb for 18 hours. The solution was acidified to pH 4 with 5N HCl and the precipitate filtered off to provide title compound (0.58 g). MS (−ve ion chemical ionisation) ml/z 152 ($[M-H]^-$, 100%).

(b) Ethyl 3-methylaminopyridazine-6-carboxylate

A solution of 3-methylaminopyridazine-6-carboxylic acid (0.58 g) in ethanol (50 ml) was saturated with HCl gas, refluxed 48 hours and evaporated. The residue was partitioned between EtOAc and aqueous $NaHCO_3$, separated and the aqueous re-extracted with EtOAc. The organic was dried and evaporated to give title compound (0.61 g). MS(+ve ion chemical ionisation) m/z 182 ($MH^+$, 100%).

(c) Ethyl 3-(N-t-butoxycarbonyl-N-methylamino) pyridazine-6-carboxylate

Preparation analogous to Preparation 9, step (a) (72%). MS (+ve ion chemical ionisation) m/z 282 ($MH^+$, 100%).

(d) Sodium 3-(N-t-butoxycarbonyl-N-methylamino) pyridazine-6-carboxylate

Preparation analogous to Preparation 4, step (c) (93%). MS (−ve ion chemical ionisation) m/z 252 ($[M-H]^-$, 100%)

Preparation 24

Sodium 6-(bis-t-butoxycarbonylamino)-5-cyanonicotinate

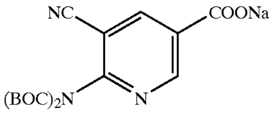

(a) 6-Hydroxy-5-iodonicotinic acid

6-Hydroxynicotinic acid (20 g) in water (200 ml) and $H_2SO_4$ (80 ml) was heated to 90° C. for 1 hour. Potassium iodate (0.42 equivalent) and potassium iodide (0.96 equivalent) were both added portionwise over 2 hours. After a further hour at 90° C. the mixture was cooled to 60° C. and added to 1 kg of ice. The brown solid was filtered off, dried and taken up in DMF (30 ml)/EtOH(1 litre). Sodium metabisulfite was added until the brown colour disappeared and the mixture was poured onto ice (2 kg), a further 1.5 litre water added and the white solid filtered to give title compound (16.5 g). NMR δ(DMSO) 12.95 (1H, broad), 12.35 (1H, broad), 8.36 (1H, d), 8.03 (1H, d)

(b) Methyl 6-chloro-5-iodonicotinate

6-Hydroxy-5-iodonicotinic acid (15.25 g) was refluxed 4 hours in thionyl chloride (40 ml)/DMF (5 ml), cooled and evaporated to dryness. The residue was taken up in chloroform (50 ml) and added to methanol (100 ml). Evaporation gave the title compound (17 g). NMR δ($CDCl_3$) 8.92 (1H, d), 8.71 (1H, d), 3.96 (3H, s).

(c) Sodium 6-chloro-5-iodonicotinate

Preparation analogous to Preparation 4, step (c) (100%). NMR δ(DMSO) 8.72 (1H, d), 8.59 (1H, d).

(d) Methyl 6-amino-5-iodonicotinate

Sodium 6-chloro-5-iodonicotinate (5 g) in 0.88 ammonia solution (125 ml) was heated at 150° C. for 18 hours in a sealed bomb, cooled and evaporated to dryness. The residue was esterified according to the procedure of Preparation 22 step (b) (2.44 g). MS (−ve ion chemical ionisation) m/z 277 ($[M-H]^-$, 100%).

(e) Methyl 6-amino-5-cyanonicotinate

A mixture of methyl 6-amino-5-iodonicotinate (2.44 g), tris(dibenzylideneacetone) dipalladium (0) (4% by weight), 1,1'-bis(diphenylphosphino)ferrocene (16% by weight) and cuprous cyanide (4 equivalents) in dioxan (50 ml) was refluxed for 4 hours, cooled and filtered. The filtrate was evaporated and the residue chromatographed, eluting with 4% $MeOH/CH_2Cl_2$ to give title compound (1.45 g). NMR δ(DMSO) 8.95 (1H, d), 8.69 (1H, d), 7.79 (2H, broad), 3.80 (3H, s).

(f) Methyl 6-(bis-t-butoxycarbonylamino)-5-cyanonicotinate

Preparation analogous to Preparation 9, step (a) (73%). NMR δ($CDCl_3$) 9.25 (1H, d), 8.60 (1H, d), 4.01 (3H, s), 1.46 (18H, s).

(g) Sodium 6-(bis-t-butoxycarbonylamino)-5-cyanonicotinate

Preparation analogous to Preparation 4, step (c) (100%). NMR δ($D_2O$) 9.03 (1H,d), 8.06 (1H, d), 1.32 (18H, s).

Pyrimidine-5-carboxylic acid was prepared according to I. T. Forbes, R. T. Martin and G. E. Jones, Preparation of indolylurea derivatives as antagonists, PCT Int. Appl. (1993) WO9318028 A1 19930916.

2-Dimethylaminopyrimidine-5-carboxylic acid was prepared according to P. Dorigo, D. Fraccarollo, G. Santostasi, I. Maragno and M. Floreani, J.Med.Chem. 39 (1996) 3671–3683.

Pyrazolo [1, 5-a] pyrimidine-3-carboxylic acid was obtained from Chembridge. 6-Dimethylaminonicotinic acid was preapred according to Tschitschibabin et. al., Chem. Ber. (1929), 62, 3052.

3-Chloropyridazine-6-carboxylic acid was prepared according to R. F. Homer, H. Gregory, W. G. Overend and L. F. Wiggins, J. Chem. Soc. (1948), 2195–2199.

EXAMPLE 1

6-Amino-3-pyridinylcarbonyl)carbamic acid 2-(S)-hydroxymutilin 14-ester

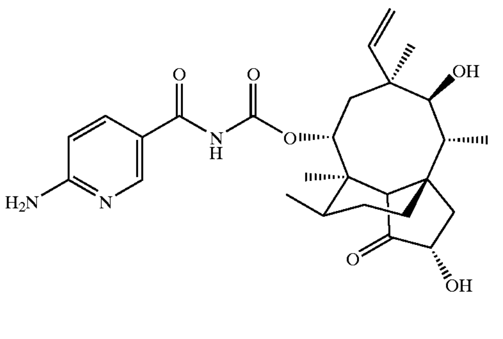

(a) (6-tert-Butyloxcarbonylamino-3-pyridinylcarbonyl) carbamic Acid-2-(S)2-dichloroacetoxymutilin 14-ester-11-trifluoroacetate

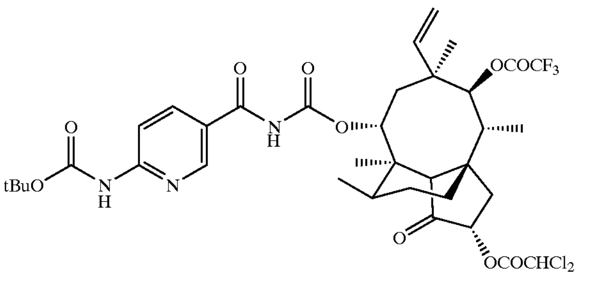

6-tert-Butyloxycarbonylaminonicotinic acid (1.0 g) in dichloromethane (100 ml) was treated with oxalyl chloride (0.44 ml) and dimethylformamide (1 drop) and stirred at ambient temperature for 3 hours. Evaporation to dryness gave the acid chloride which was dissolved in dichloromethane (150 ml) and treated with silver cyanate (1.0 g, 6.7 mmoles), 2-(S)-2-dichloroacetoxymutilin 11-trifluoroacetate (2.3 g) and triethylamine (0.65 ml) and stirred at ambient temperature for 18 hours. Filtration and evaporation of the filtrate to dryness followed by chromatography on silica gel, eluting with 25% ethyl acetate in hexane gave the title compound as a white foam (0.53 g, 15%).

(b) (6-tert-Butyloxycarbonylamino-3-pyridinylcarbonyl) carbamic Acid 2-(S)-hydroxymutilin 14-ester

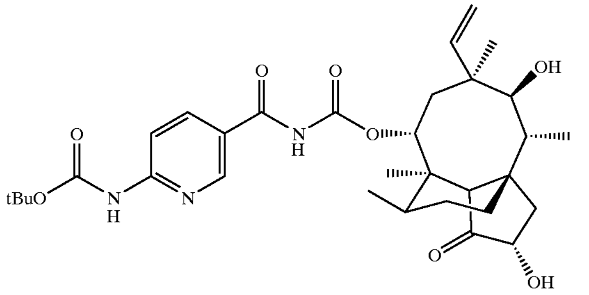

(6-tert-Butyloxycarbonylamnino-3-pyridinylcarbonyl) carbamic acid 2-(S)-2-dichloroacetoxy-mutilin 14-ester-11-trifluoroacetate (0.52 g) in absolute ethanol (20 ml) was treated with 0.5N potassium hydroxide in ethanol solution (2.5 ml, 1.2 mmoles) and stirred at ambient temperature for 4 hours. The mixture was evaporated to dryness and the residue partitioned between water and ethyl acetate. The organics were separated, dried ($Na_2SO_4$) filtered and evaporated to dryness to give the title compound (0.37 g, 100%).

(c) (6-Amino-3-pyridinylcarbonyl)carbamic Acid 2-(S)-hydroxymutilin 14-ester

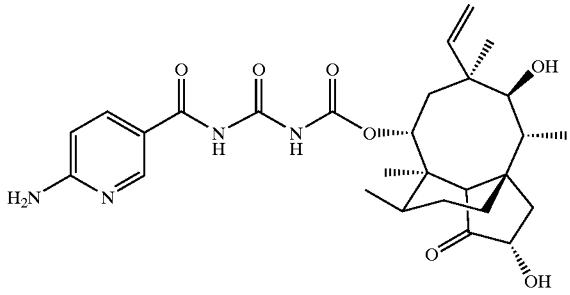

(6-tert-Butyloxycarbonylamino-3-pyridinylcarbonyl) carbamic acid 2-(S)-hydroxymutilin 14- ester(0.37 g) in dichloromethane (50 ml), was treated with trifluoroacetic acid (2 ml) and stirred at ambient temperature for 5 hours. The mixture was evaporated to dryness and the residue partitioned between 10% potassium carbonate solution and 10% methanol/dichloromethane (2×100 ml). The organics were separated, dried ($Na_2SO_4$), filtered and evaporated to dryness. Chromatography on silica gel, eluting with 8% methanol/dichloromethane gave the title compound as a white solid (0.117 g, 37%). M.S. (−ve ion electrospray) m/z 498 ($[M-H]^-$, 30%), 161 (100%).

EXAMPLES 2–27

(a) The following were prepared analogously to step (a) of example 1

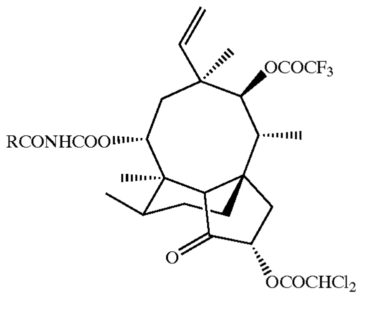

| Example No. | R | % yield | Electrospray MS m/z |
|---|---|---|---|
| 2 | 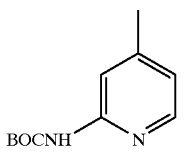 | 20 | |

-continued
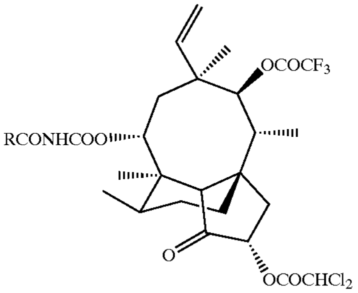
| Example No. | R | % yield | Electrospray MS m/z |
|---|---|---|---|
| 3 | 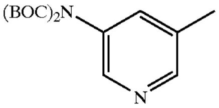 | 26 | (−ve ion) 904 ([M − H]$^-$, 100%) |
| 4 | 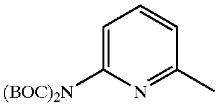 | 54 | (−ve ion) 904 ([M − H]$^-$, 100%) |
| 5 | 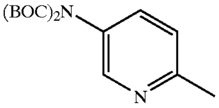 | 39 | (−ve ion) 904 ([M − H]$^-$, 100%) |
| 6 | 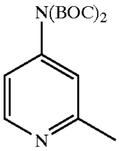 | 44 | (−ve ion) 904 ([M − H]$^-$, 100%) |
| 7 | 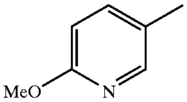 | 54 | (−ve ion) 719 ([M − H]$^-$, 100%) |
| 8 | 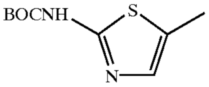 | 40 | (−ve ion) 810 ([M − H]$^-$, 100%) |
| 9 | 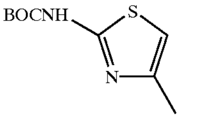 | 34 | (−ve ion) 810 ([M − H]$^-$, 100%) |
| 10 | 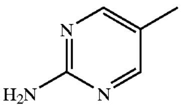 | 12 | |
| 11 | 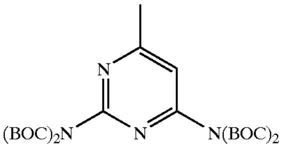 | 62 | |
| 12 | 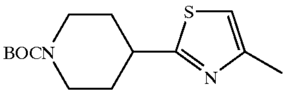 | 71 | (+ve ion) 902 ($MNa^+$, 20%) 880($MH^+$, 20%)212(100%) |

-continued
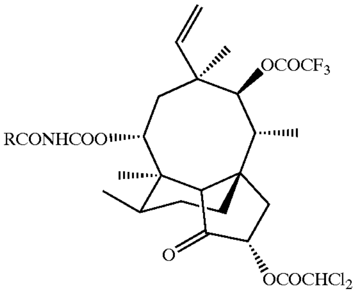
| Example No. | R | % yield | Electrospray MS m/z |
|---|---|---|---|
| 13 | 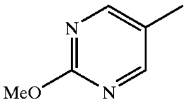 | 42 | (−ve ion)720([M − H]⁻, 65%, 113(100%) |
| 14 | 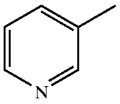 | 20 | |
| 15 | 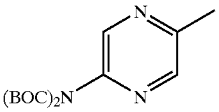 | 83 | (−ve ion) 905 ([M − H]⁻, 40%), 113 (100%) |
| 16 | 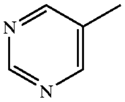 | 18.5 | (−ve ion) 690 ([M − H]⁻, 90%), 123 (100%) |
| 17 | 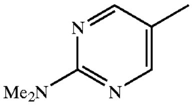 | 49 | (−ve ion) 733 ([M − H]⁻, 100%) |
| 18 | 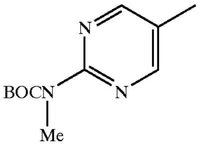 | 18 | (−ve ion) 819 ([M − H]⁻, 100%) |
| 19 | 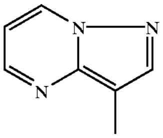 | 44 | (−ve ion) 729 ([M − H]⁻, 100%) |
| 20 | 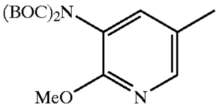 | 15 | (−ve ion) 934 ([M − H]⁻, 100%) |
| 21 | 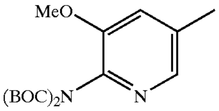 | 44 | |

-continued
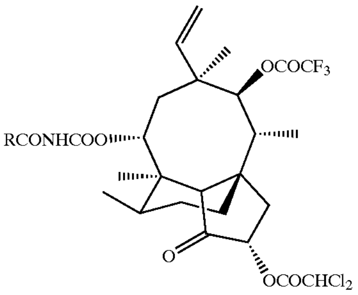
| Example No. | R | % yield | Electrospray MS m/z |
|---|---|---|---|
| 22 | 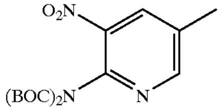 | 68 | |
| 23 | 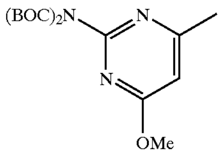 | — | |
| 24 | 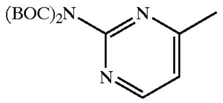 | 59 | |
| 25 | 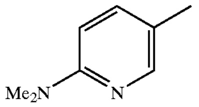 | 15 | (+ve ion) 734 ($MH^+$, 100%) |
| 26 | 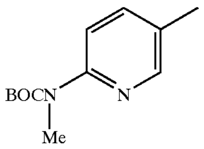 | 66 | (–ve ion) 818 ($[M-H]^-$, 100%) |
| 27 | 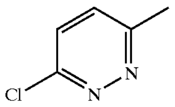 | 76 | |
| 28 | 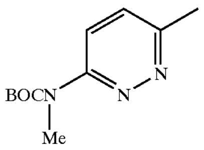 | 29 | (–ve ion) 819 ($[M-H]^-$, 100%) |
| 29 | 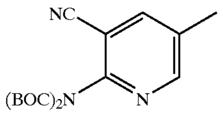 | 16 | (–ve ion) 929 ($[M-H]^-$, 100%) |

2-Aminopyrimidin-5-ylcarbonyl chloride hydrochloride for example 10 was prepared by reflux of 2-aminopyrimidin-5-yl carboxylic acid (0.4 g) (P. Schenone et. al., J.Heterocyclic Chem. 27 (1990)295) in thionyl chloride (20 ml) for 4 hours followed by evaporation to dryness.

EXAMPLE 3

(b) (5-Bis-t-butoxycarbonylaminonicotinoyl)carbamic Acid 2-(S)-hydroxymutilin 14-ester A solution of (5-bis-t-butoxycarbonylaminonicotinoyl) carbamic acid 2-(S)-dichloroacetoxymutilin 14-ester-11- trifluororacetate (0.25 g) in ethanol (25 ml) was treated with saturated aqueous $NaHCO_3$ (25 ml) and stirred vigorously for 2½ hours. The mixture was diluted with EtOAc (150 ml) and water (150 ml), shaken and separated. The organic was dried and evaporated to give the title compound as a white solid (0.198 g). MS(−ve ion electrospray) m/z 698 ([M-H]$^-$, 100%).

EXAMPLES 2,4–17, 19–21 and 24–26

(b) The following were prepared analogously to step (b) of either Example 1 or Example 3.

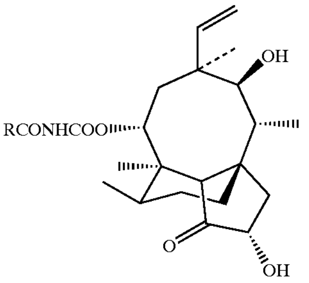

| Example No. | R | % yield | Electrospray MS m/z |
|---|---|---|---|
| 2 | 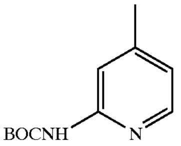 | 100 | |
| 4 | 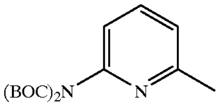 | 100 | |
| 5 | 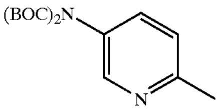 | 62 | (−ve ion) 698 ([M − H]$^-$, 100%) |
| 6 | 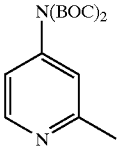 | 76 | (−ve ion) 698 ([M − H]$^-$, 100%) |
| 7 | 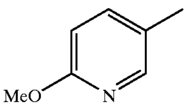 | 45 | (−ve ion) 513 ([M − H]$^-$, 100%) |
| 8 | 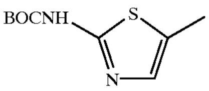 | 97 | (−ve ion) 604 ([M − H]$^-$, 100%) |
| 9 | 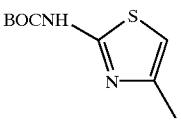 | 97 | |

-continued
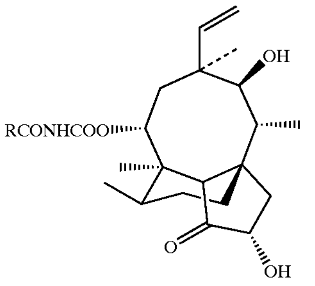
| Example No. | R | % yield | Electrospray MS m/z |
|---|---|---|---|
| 10 | 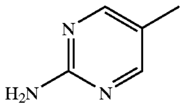 | 62 | (−ve ion) 499 ([M − H]$^-$, 100%) |
| 11 | 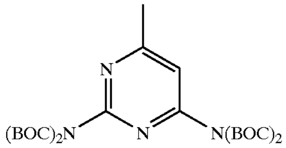 | 100 | |
| 12 | 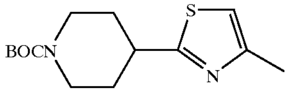 | 99 | (−ve ion) 672 ([M − H]$^-$, 100%) |
| 13 | 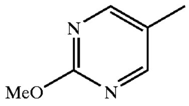 | 69 | (−ve ion) 514 ([M − H]$^-$, 100%) |
| 14 | 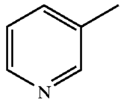 | 18 | (+ve ion) 991 (2MNa$^+$, 100%), 485 (MH$^+$, 40%) |
| 15 | 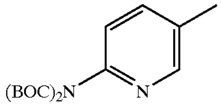 | 18 | (−ve ion) 699 ([M − H]$^-$, 100%) |
| 16 | 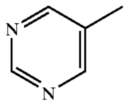 | 11 | (−ve ion) 484 ([M − H]$^-$, 60%), 122 (100%) |
| 17 | 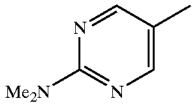 | 97 | (−ve ion) 527 ([M − H]$^-$, 100%) |
| 19 | 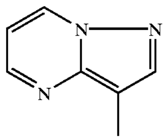 | 70 | (−ve ion) 523 ([M − H]$^-$, 100%) |
| 20 | 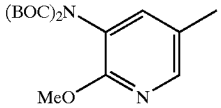 | 100 | |

-continued

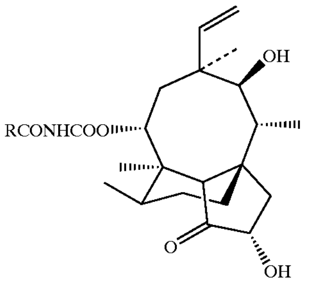

| Example No. | R | % yield | Electrospray MS m/z |
|---|---|---|---|
| 21 | 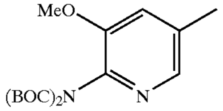 | 100 | |
| 24 | 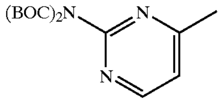 | 27 | |
| 25 | 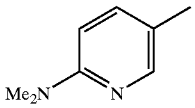 | 54 | (+ve ion) 528 ($MH^+$, 100%) |
| 26 | 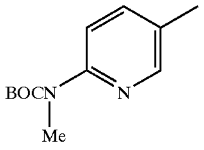 | 91 | (−ve ion) 612 ($[M-H]^-$, 100%) |

EXAMPLE 3

(c) (5-Aminonicotinoyl)carbamic Acid 2-(S)hydroxymutilin 14-ester

A solution of (5-bis-t-butoxycarbonylaminonicotinoyl) carbamic acid 2-(S)-hydroxymutilin 14-ester (0.198 g) in trifluoroacetic acid (2 ml) was kept for 1 hour and evaporated. The residue was treated with EtOAc (10 ml) and saturated aqueous $NaHCO_3$ (10 ml), shaken and separated. The organic was dried and evaporated. Chromatography (EtOAc/MeOH) gave the title compound (0.084 g). MS (−ve ion electrospray) m/z 498 ($[M-H]^-$, 100%).

EXAMPLES 2,4–6, 8–9, 11–12, 15, 20–21, 24 and 26

(c) The following were prepared analogously to step (c) of either example 1 or example 3

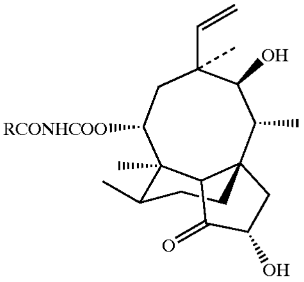
| Example No. | R | % yield | Electrospray MS m/z |
|---|---|---|---|
| 2 | 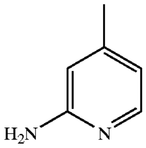 | 20 | (−ve ion) 498 ([M − H]$^-$, 38%), 268 (100%) |
| 4 | 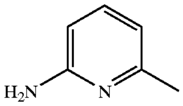 | 85 | (−ve ion) 498 ([M − H]$^-$, 100%) |
| 5 | 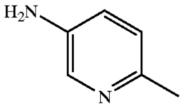 | 77 | (−ve ion) 558(MOAc$^-$, 40%), 498([M − H]$^-$, 85%), 162 (100%) |
| 6 | 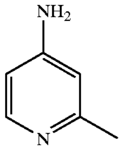 | 68 | (−ve ion) 498 ([M − H]$^-$, 70%), 162 (100%) |
| 8 | 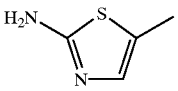 | 90 | (−ve ion) 504 ([M − H]$^-$, 30%), 168 (100%) |
| 9 | 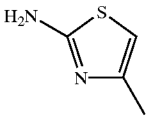 | 85 | (−ve ion) 504 ([M − H]$^-$, 10%), 168 (100%) |
| 11 | 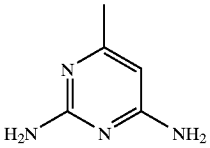 | 30 | (−ve ion) 514 ([M − H]$^-$, 55%), 178 (100%) |
| 12 | 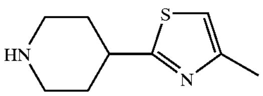 | 71 | (−ve ion) 572 ([M − H]$^-$, 100%) |
| 15 | 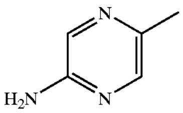 | 61 | (−ve ion) 499 ([M − H]$^-$, 55%), 163 (100%) |

-continued

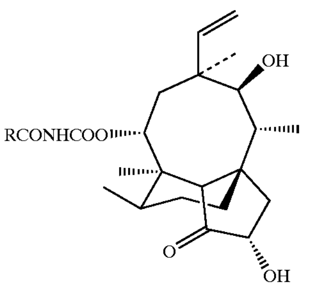

| Example No. | R | % yield | Electrospray MS m/z |
|---|---|---|---|
| 20 | 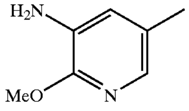 | 49 | (−ve ion) 528 ([M − H]$^-$, 100%) |
| 21 | 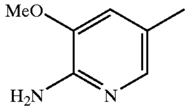 | 65 | (−ve ion) 528 ([M − H]$^-$, 100%) |
| 24 | 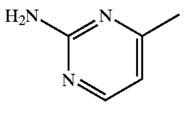 | 94 | (−ve ion) 499 ([M − H]$^-$, 100%) |
| 26 | 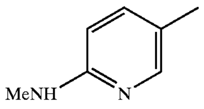 | 30 | (−ve ion) 512 ([M − H]$^-$, 100%) |

EXAMPLE 18

(2-N-methylaminopyrimidin-5-ylcarbonyl)carbamic Acid 2-(S)-hydroxymutilin 14-ester (b) (2-N-methylaminopyrimidin-5-ylcarbonyl)carbamic Acid 2-(S)-dichloroacetoxy-11-O-trifluoroacetylmutilin 14-ester BOC-protected material from step (a) (see table) was deprotected with TFA using the procedure of Example 3, step (c) (100%). MS (−ve ion electrospray) m/z 719 ([M-H]$^-$, 100%).

(c) (2-N-methylaminopyrimidin-5-ylcarbonyl)carbamic Acid 2-(S)-hydroxymutilin 14-ester Material from step (b) was treated according to the procedure of Example 3, step (b) to give the title compound (64%). MS (+ve ion electrospray) m/z 515 (MH$^+$, 100%)

EXAMPLE 22(b)

(6-Amino-5-nitronicotinoyl)carbamic Acid 2-(S)-hydroxymutilin 14-ester

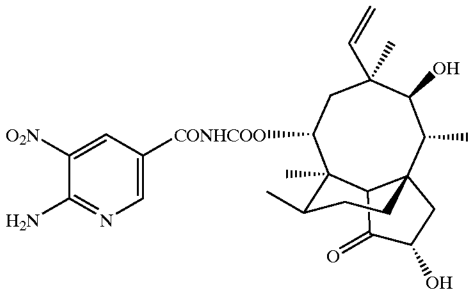

(6-Bis-t-butoxycarbonylamino-5-nitronicotinoyl) carbamic Acid 2-(S)-dichloroacetoxy-11-O-trifluoroacetylmutilin (see table) was treated with TFA according to Example 3, step (c) followed by base according to Example 3, step (b) to give the title compound (95%), MS (−ve ion chemical ionisation) m/z 543 ([M-H]$^-$, 100%).

EXAMPLE 23(b)

(2-Amino-6-methoxypyrimidin-4-ylcarbonyl) carbamic Acid 2-(S)-hydroxymutilin 14-ester

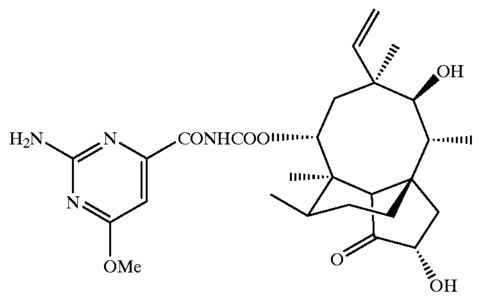

(2-Bis-t-butoxycarbonylamino-6-methoxypyrimidin-4-ylcarbonyl)carbamic acid 2-(S)-dichloroacetoxy-11-O-trifluoroacetylmutilin (see table) was treated with TFA according to Example 3, step (c) followed by base according to Example 3, step (b) to give the title compound. MS (−ve ion electrospray) m/z 529 ($[M-H]^-$, 60%), 193 (100%).

EXAMPLE 27

(3-Amino-6-pyridazinylcarbonyl)carbamic Acid 2-(S)-hydroxymutilin 14-ester Hydrochloride

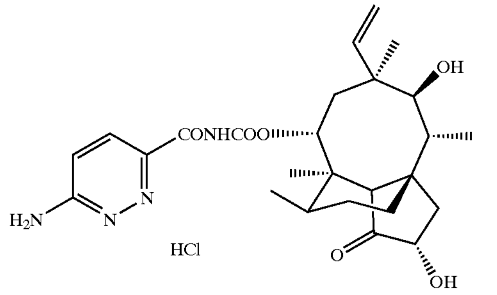

(b) (Tetrazolo [1,5-b] pyridazin-6-ylcarbonylcarbamic Acid (2S)-2-dichloroacetoxy-11-O-trifluoroacetylmutilin 14-ester

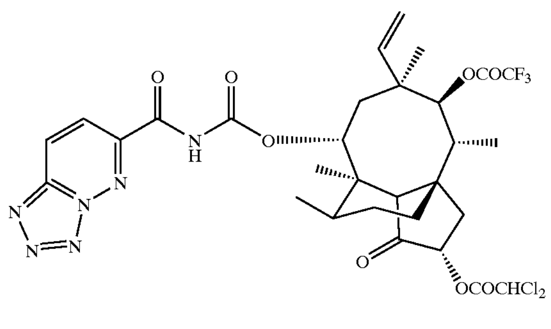

The title compound was prepared from 1-(3-chloro-6-pyridazinylcarbonyl)carbamic acid (2S)-2-dichloroacetoxy-11-O-trifluoroacetyl mutilin 14-ester (see table) (1.5 g) by treatment with sodium azide (0.162 g) in DMF (20 ml) at ambient temperature for 4 hours. The mixture was then evaporated to dryness and the residue extracted with ethyl acetate (50 ml) and washed with water (3x50 ml), dried and evaporated to give (1.02 g, 70%). M.S. (−ve ion electrospray) m/z 731 ($[M-H]^-$, 15%), 164 (100%).

(c) (3-Triphenylphosphoranylideneamino-6-pyridazinyl carbonyl)carbamic Acid (2S)-2-dichloroacetoxy-11-O-trifluoroacetylmutilin 14-ester.

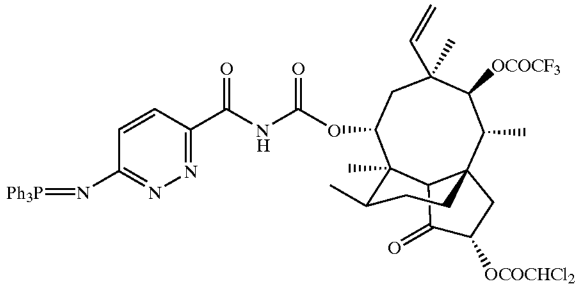

(Tetrazolo [1,5-b] pyridazin-6-ylcarbonyl)carbamic acid-(2S)-2-dichloroacetoxy-11-O-trifluoroacetylmutilin 14-ester (0.45 g) was heated in chlorobenzene (10 ml) with triphenylphosphine (0.165 g) at 110° C. for 18 hours. Evaporation followed by chromatography on silica gel eluting with 50% ethyl acetate in hexane gave the title compound (0.255 g, 43%). M.S. (+ve ion electrospray) m/z 967 ($MH^+$, 80%), 839 (100%).

(d) (3-Amino-6-pyridazinylcarbonyl)carbamic Acid-(2S)-2-dichloroacetoxy-11-O-trifluoroacetylmutilin 14-ester

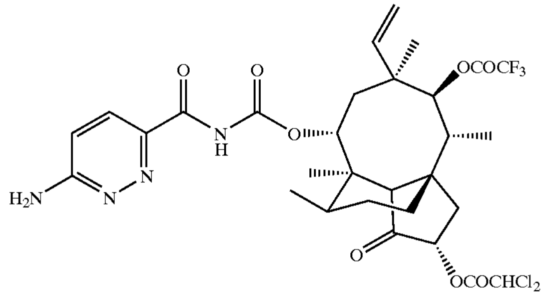

(3-Triphenylphosphoranylideneamino-6-pyridazinylcarbonyl)carbamic acid-(2S)-2-dichloroacetoxy-11-O-trifluoroacetylmutilin 14-ester (0.25 g) was treated with glacial acetic acid (5 ml) and water (0.5 ml) and heated at 100° C. for 1 hour. The mixture was evaporated to dryness and the residue extracted with ethyl acetate and washed with saturated aqueous sodium bicarbonate solution, dried and evaporated to dryness to give the title compound as a 1:1 mixture with triphenylphosphine oxide (0.23 g, 88%). M.S (−ve ion electrospray) m/z 705 ($[M-H]^-$, 18%), 375 (100%).

(e) (3-Amino-6-pyridazinylcarbonyl)carbamic Acid-(2S)-2-hydroxymutilin 14-ester Hydrochloride (3-Amino-6-pyridazinylcarbonyl)carbamic acid-(2S)-2-dichloroacetoxy-11-O-trifluoro acetyl mutilin 14-ester (0.23 g) was treated with aqueous sodium bicarbonate as in Example 3, step (b) then treated with ethereal hydrogen chloride to give the title compound (0.05 g, 41%). M.S. (−ve ion electrospray) m/z 499 ($[M-H]^-$, 100%).

EXAMPLE 28

(3-N-methylpyridazin-6-ylcarbonyl)carbamic Acid 2-(S)-hydroxymutilin 14-ester (b) (3-N-methylpyridazin-6-ylcarbonyl) Carbamic Acid 2-(S)-dichloroacetoxy-11-O-trifluoroacetylmutilin 14-ester BOC-protected material from step (a) (see table) was deprotected with TFA using the procedure of Example 3, step (c) (73%). MS (−ve ion electrospray) m/z 720 ($[M-H]^-$, 100%).

(c) (3-N-methylpyridazin-6-ylcarbonyl)carbamic Acid 2-(S)-hydroxymutilin 14-ester Material from step (b) was treated according to the procedure of Example 3, step (b) to give the title compound (44%). MS (−ve ion electrospray) m/z 513 ([M-H]$^-$,100%).

EXAMPLE 29

(6-Amino-5-cyanonicotinoyl)carbamic Acid 2-(S)-hydroxymutilin 14-ester (b) (6-Amino-5-cyanonicotinoyl)carbamic Acid 2-(S)-dichloroacetoxy-11-O-trifluoroacetylmutilin 14-ester BOC-protected material from step (a) (see table) was deprotected with TFA using the procedure of Example 3, step (c) (76%). MS (−ve ion electrospray) m/z 729 ([M-H]$^-$, 100%).

(c) (6-Amino-5-cyanonicotinoyl)carbamic Acid 2-(S)-hydroxymutilin 14-ester

Material from step (b) was treated according to the preocedure of Example 3, step (b) to give the title compound (60%). MS (−ve ion electrospray) m/z 523 ([M-H]$^-$, 100%).

EXAMPLE 30

[2-(1-Carboxamidomethylpiperidin-4-yl) thiazole-4-carbonyl]carbamic Acid 2-(S)-hydroxymutilin 14-ester

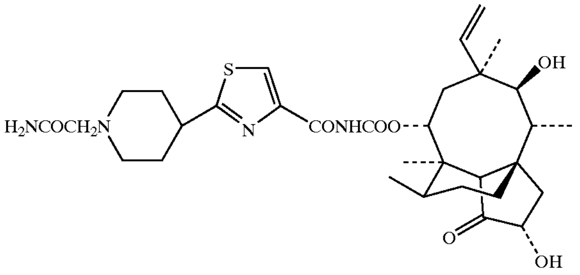

A solution of [2-(piperidin-4-yl)thiazole-4-carbonyl] carbamic acid 2-(S)-hydroxymutilin 14-ester (example 12, 120 mg) in acetonitrile (3.5 ml)/DMF (0.5 ml) was treated with potassium carbonate (73 mg) and 2-bromoacetamide (29 mg) and stirred overnight. The mixture was diluted with EtOAc (10 ml), washed with water (3x10 ml), dried and evaporated. Chromatography, eluting with chloroform/methanol/0.88$NH_3$ (aq) 94:6:0.6 gave the title compound (90 mg). MS (+ve ion electrospray)m/z 631 (MH$^+$,30%), 269 (100%).

EXAMPLE 31

[2-(1-Cyanomethylpiperidin-4-yl)thiazole-4-carbonyl]carbamic Acid 2-(S)-hydroxymutilin 14-ester Using bromacetonitrile as alkylating agent, an analogous reaction to that of example 30 gave the title compound (74%) MS(−ve ion electrospray) m/z 611 ([M-H]$^-$,100%).

EXAMPLE 32

(6-aminopyridin-2-ylcarbonyl)carbamic Acid 19,20-dihydro-2-(S)-hydroxymutilin 14-ester

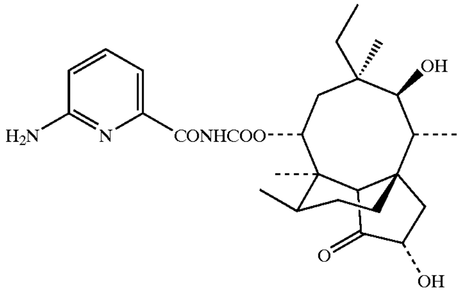

A solution of (6-aminopyridin-2-ylcarbonyl)carbamic acid 2-(S)-hydroxymutilin 14-ester (Example 4) (150 mg) in ethanol (20 ml) was treated with 10% Pd/C (50 mg) and stirred under hydrogen at atmospheric pressure overnight. The catalyst was filtered off and the filtrate evaporated to give the title compound (130 mg). MS (+ve ion electrospray) m/z 502 (, 40%), 524 (MNa$^+$, 65%), 565 (100%).

EXAMPLE 33

(6-Amino-5-cyanonicotinoyl)carbamic Acid 19,20-dihydro-2-(S-hydroxymutilin 14-ester (6-Amino-5-cyanonicotinoyl)carbamic acid 2-(S)-hydroxymutilin 14-ester was hydrogenated according to the procedure of example 32 (but using dioxan as solvent instead of EtOH) to give title compound (62%). MS (−ve ion electrospray) m/z 525 ([M-H]$^-$, 100%).

EXAMPLE 34

(3-Oxo-3,4-dihydropyrido[2,3-b]pyrazin-7-ylcarbonyl)carbamic Acid 19,20-dihydro-2-(S)-hydroxymutilin 14-ester

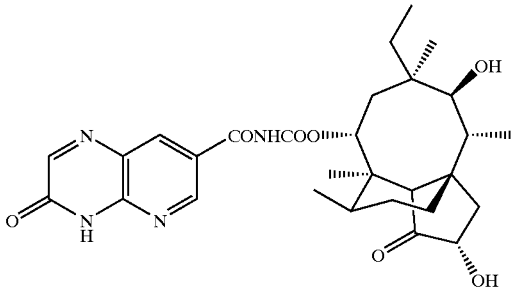

(a) (5,6-Diaminonicotinoyl)carbamic Acid 19,20-dihydro-2-(S)-hydroxymutilin 14-ester (6-Amino-5-nitronicotinoyl)carbamic acid 2-(S)-hydroxymutilin 14-ester (Example 22) was hydrogenated according to the procedure of Example 32 to give the title compound (86%). MS (+ve ion chemical ionisation) m/z 517 (MH$^+$, 100%).

(b) (3-Oxo-3,4-dihydropyrido[2,3-b]pyrazin-7-ylcarbonyl) carbamic Acid 19,20-dihydro-2-(S)-hydroxymutilin 14-ester A solution of (5,6-diaminonicotinoyl)carbamic acid 19,20-dihydro-2-(S)-hydroxymutilin 14-ester (118 mg) in ethanol (10 ml) was treated with a solution of ethylglyoxylate (150 ml of 4.9 M toluene solution) and heated to 50° C. for 3 hours. Solvent was evaporated and the residue chromatographed, eluting with dichloromethane/methanol 97:3 to give the title compound (13 mg). MS (+ve ion chemical ionisation) m/z 555 ($MH^+$, 100%).

EXAMPLE 35

(2-Aminothiazol-5-ylcarbonyl)carbamic Acid 19,20-dihydro-2-(S)-hydroxymutilin 14-ester

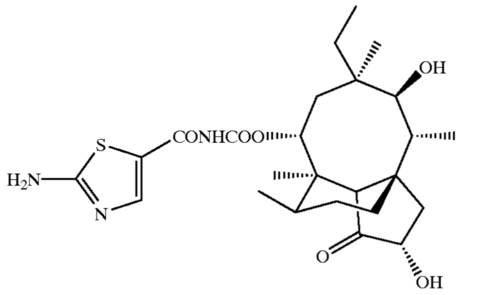

(a) (2-t-Butoxycarbonylaminothiazol-5-ylcarbonyl) carbamic Acid 19,20-dihydro-2-(S)-hydroxymutilin 14-ester (2-t-Butoxycarbonylaminothiazol-5-ylcarbonyl)carbamic acid-2-(S)-hydroxymutilin 14-ester (example 8, step (b))) was hydrogenated as described in Example 32 to give the title compound (46%). MS (−ve ion electrospray) m/z 606 ($[M-H]^-$, 50%/), 268 (100%).

(b)) (2-Aminothiazol-5-ylcarbonyl)carbamic acid 19,20-dihydro-2-(S)-hydroxymutilin 14-ester BOC-protected compound from step (a) was deprotected as described in Example 3 step (c) to give the title compound (46%). MS (−ve ion electrospray) m/z 506 ($[M-H]^-$, 100%).

EXAMPLE 36

(5-Amino-6-methoxynicotinoyl)carbamic Acid 19, 20-dihydro-2-(S)-hydroxymutilin 14-ester

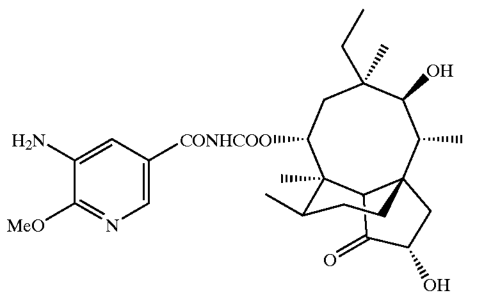

(5-Amino-6-methoxynicotinoyl)carbamic acid 2-(S)-hydroxymutilin 14-ester was hydrogenated as described in example 32 to give the title compound. MS (−ve ion electrospray) m/z 530 ($[M-H]^-$, 50%), 192 (100%).

EXAMPLES 37–39

(a) The following were prepared analogously to step (a) of Example 1, using 2-(S)-2-dichloroacetoxy-19,20-dihydro-11-O-tifluoroacetylmutilin (Preparation 14).

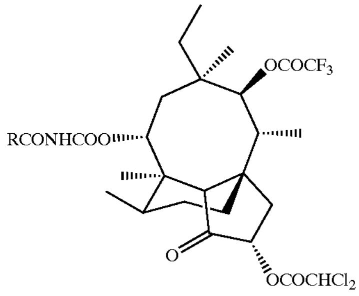

| Example No | R | % yield | Electrospray MS m/z |
|---|---|---|---|
| 37 | 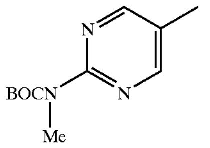 | 18 | (−ve ion) 821 ($[M-H]^-$, 100%) |
| 38 | 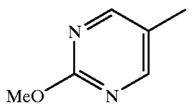 | 28 | (−ve ion) 722 ($[M-H]^-$, 100%) |
| 39 | 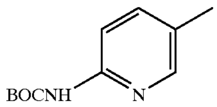 | 16 | |

EXAMPLE 37(b)

(2-Methylaminopyrimidin-5-ylcarbonyl)carbamic Acid 19,20-dihydro-2-(S)-hydroxymutilin 14-ester

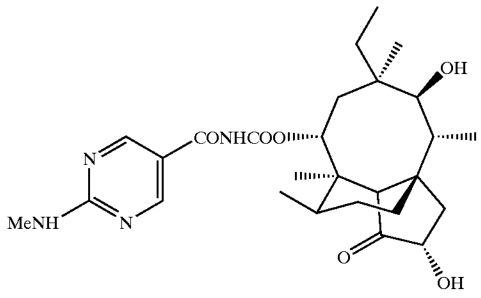

(2-N-t-butoxycarbonyl-N-methylaminopyrimidin-5-ylcarbonyl)carbamic acid 2-(S)-dichloracetoxy-19,20-dihydro-11-O-trifluoroacetylmutilin 14-ester (see table) was treated with TFA according to the procedure of Example 3, (step (c) (100%). [MS (−ve ion electrospray) m/z 721 ($[M-H]^-$, 100%)] and then with base according to the procedure of Example 3, step (b) (44%). MS (−ve ion electrospray) m/z 515 ($[M-H]^-$, 100%)

EXAMPLE 38 (b)

(2-Methoxypyrimidin-5-ylcarbonyl)carbamic Acid 19,20-dihydro-2-(S)-hydroxymutilin 14-ester

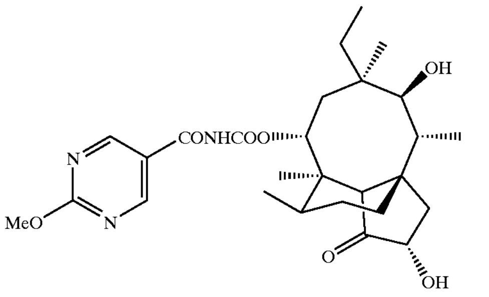

(2-Methoxypyrimidin-5-ylcarbonyl)carbamic acid 2-(S)-dichloroacetoxy-19,20-dihydro-11-O-trifluoroacetylmutilin 14-ester was deprotected according to the procedure of Example 3, step (b) to provide the title compound (43%). MS (+ve ion electrospray) 518 ($MH^+$, 100%).

EXAMPLE 39 (b)

(6-Aminonicotinoyl)carbamic Acid 19,20-dihydro-2-(S)-hydroxymutilin 14-ester

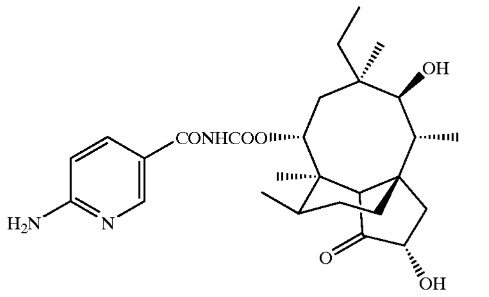

(6-t-Butoxycarbonylaminonicotinoyl)carbamic acid 2-(S)-dichloroacetoxy-19,20-dihydro-11-O-trifluoroacetylmutilin 14-ester (see table) was deprotected according to the procedure of Example 3, step (b) (65%) [MS (−ve ion chemical ionisation) m/z 600 ($[M-H]^-$, 100%)] and then according to Example 3, step (c) (39%). MS (−ve ion electrospray) m/z 500 ($[M-H]^-$, 100%).

Biological Data

Compounds of the present invention were assessed for anti-bacterial activity in a conventional MIC assay against a range of pathogenic organisms.

Examples 1 to 39 were found to have MICs ≦4 μg/ml against *Staphylococcus aureus* Oxford, *Streptococcus pneumoniae* 1629, *Moraxella catarrhalis* Ravasio, and *Haemophilius influenzae* Q1.

The improved stability of the 2S-hydroxy compounds was demonstrated using human liver microsome preparations. Thus, for the compounds in which $R^1$=2-amino-4-pyridyl and $R^2$=vinyl, the intrinsic clearances (CLi, a measure of rate of metabolism) in the presence of human liver microsomes were found to be: 2α-H, CLi>50 ml/min/g liver; 2α-OH, CLi=6.5 ml/min/g liver.

What is claimed is:

1. A compound of Formula (I):

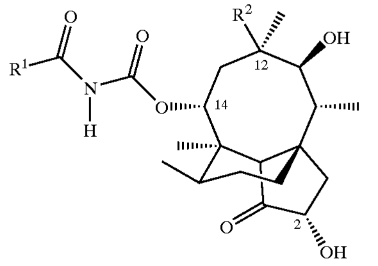

(I)

in which:

$R^1$ is an optionally substituted pyridine; and $R^2$ is vinyl or ethyl; or a pharmaceutically acceptable salt thereof.

2. A compound of formula (I) as claimed in claim 1 in which substituents for $R^1$ are selected from amino, mono- or di-($C_{1-6}$)alkylamino, ($C_{1-6}$)alkyl, ($C_{1-6}$)alkoxy, nitro and N-containing heterocyclyl; or a pharmaceutically acceptable salt thereof.

3. A compound of formula (I) as defined in claim 1 selected from the group consisting of:

(6-Amino-3-pyridinylcarbonyl)carbamic acid 2-(S)-hydroxymutilin 14-ester;

(5-Aminonicotinoyl)carbamic acid 2-(S)-hydroxymutilin 14-ester;

(6-Amino-5-cyanonicotinoyl)carbamic acid 2-(S)-hydroxymutilin 14-ester;

(6-aminopyridin-2-ylcarbonyl)carbamic acid 19,20-dihydro-2-(S)-hydroxymutilin 14-ester;

(6-Amino-5-cyanonicotinoyl)carbamic acid 19,20-dihydro-2-(S)-hydroxymutilin 14-ester;

(5-Amino-6-methoxynicotinoyl)carbamic acid 19,20-dihydro-2-(S)-hydroxymutilin 14-ester;

(6-Amino-5-nitronicotinoyl)carbamic acid 2-(S)-hydroxymutilin 14-ester; and;

a compound of formula (I) in which $R^2$ is ethyl and $R^1$ is selected from:

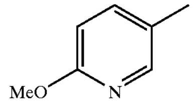 , 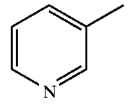 ,

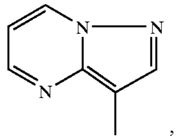 , 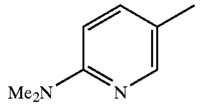 ,

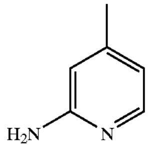 , 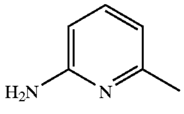 ,

-continued

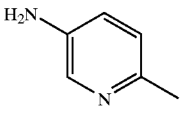 , 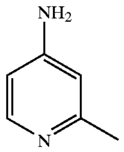 ,

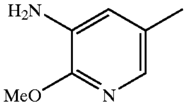 , 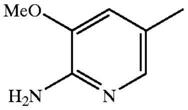 , and

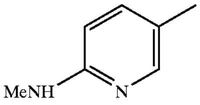 ;

wherein Me is methyl; or a pharmaceutically acceptable salt thereof.

4. A compound of formula (I) as defined in claim 1 selected from the group consisting of:

(5-Amino-6-methoxy-3-pyridinylcarbonyl)carbamic acid 2-(S)-hydroxymutilin 14-ester;

(5-Amino-6-methoxy-3-pyridinylcarbonyl)carbamic acid 19,20-dihydro-2-(S)-hydroxymutilin 14-ester;

(6-Amino-3-pyridinylcarbonyl)carbamic acid 19,20-dihydro-2-(S)-hydroxymutilin 14-ester; and (6-Dimethylamino-3-pyridinylcarbonyl)carbamic acid 2-(S)-hydroxymutilin 14-ester; or a pharmaceutically acceptable salt thereof.

5. A pharmaceutical composition comprising a compound of formula (I) as claimed in claim 1; or a pharmaceutically acceptable salt thereof; and a pharmaceutically acceptable carrier or excipient.

6. A method of treating bacterial-infections in animals, including humans, which comprises administering an effective amount of a compound as claimed in claim 1; or a pharmaceutically acceptable salt thereof; to a patient in need thereof.

7. A process for preparing a compound of formula (I) as claimed in claim 1; or a pharmaceutically acceptable salt thereof; which process comprises reacting a compound of formula (II):

(II)

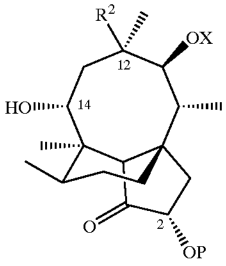

in which X and P are hydrogen or a hydroxyl protecting group, and $R^2$ is as defined in claim 1; with an acyl isocyanate of formula $R^{1A}CONCO$ in which $R^{1A}$ is $R^1$ as hereinbefore defined or a group convertible into $R^1$, and thereafter and if necessary:

(a) deprotecting a group P and/or X to generate a hydroxyl group at position 2 or 11, respectively, (b) converting a group $R^{1A}$ to $R^1$, for instance removing a protecting group, (c) converting a group $R^1$ to another group $R^1$, and (d) hydrogenating the vinyl group at position 12 to form an ethyl group.

8. A compound of formula (I) as defined in claim 1 which is (5-amino-6-methoxy-3-pyridinylcarbonyl)carbamic acid 2-(S)-hydroxymutilin 14-ester, or a pharmaceutically acceptable salt thereof.

9. A compound of formula (I) as defined in claim 1 which is (5-amino-6-methoxy-3-pyridinylcarbonyl)carbamic acid 2-(S)-hydroxymutilin 14-ester.

* * * * *